(12) United States Patent  
Song et al.

(10) Patent No.: US 9,562,024 B2  
(45) Date of Patent: Feb. 7, 2017

(54) VORTIOXETINE SALT AND CRYSTAL THEREOF, THEIR PREPARATION METHOD, PHARMACEUTICAL COMPOSITIONS AND USAGE

(71) Applicant: HANGZHOU PUSHAI PHARMACEUTICAL TECHNOLOGY CO., LTD, Hangzhou (CN)

(72) Inventors: Xiaoye Song, Hangzhou (CN); Xiaoxia Sheng, Hangzhou (CN); Xiaohong Sheng, Hangzhou (CN)

(73) Assignee: HANGZHOU PUSHAI PHARMACEUTICAL TECHNOLOGY CO., LTD, Hangzhou (CN)

( * ) Notice: Subject to any disclaimer, the term of this patent is extended or adjusted under 35 U.S.C. 154(b) by 0 days.

(21) Appl. No.: 15/048,868

(22) Filed: Feb. 19, 2016

(65) Prior Publication Data  
US 2016/0214950 A1    Jul. 28, 2016

Related U.S. Application Data

(63) Continuation of application No. PCT/CN2014/079346, filed on Jun. 6, 2014.

(30) Foreign Application Priority Data

Sep. 12, 2013  (CN) .......................... 2013 1 0415148

(51) Int. Cl.  
   *C07D 295/096*   (2006.01)  
(52) U.S. Cl.  
   CPC ................. *C07D 295/096* (2013.01)  
(58) Field of Classification Search  
   CPC .................................. C07D 295/096  
   USPC ..................................................... 514/255.03  
   See application file for complete search history.

(56) References Cited

U.S. PATENT DOCUMENTS 8,722,684 B2 *   5/2014   Bang-Andersen . C07D 295/096  
                                                                424/489

FOREIGN PATENT DOCUMENTS

| CN | 101472906 A | 7/2009 |
| CN | 101636161 A | 1/2010 |
| CN | 102317272 A | 1/2012 |

OTHER PUBLICATIONS

International Search Report for PCT/CN2014/079346 mailed Sep. 17, 2014.  
Written Opinion for PCT/CN2014/079346 mailed Sep. 17, 2014.  
International Preliminary Report on Patentability issued Mar. 15, 2016.

* cited by examiner

*Primary Examiner* — San-Ming Hui  
(74) *Attorney, Agent, or Firm* — Duane Morris LLP

(57) ABSTRACT

The present invention relates to the novel vortioxetine salts, solvates and crystalline forms thereof, specifically, vortioxetine hemihydrobromide and a crystalline form thereof, and isopropanol solvate of vortioxetine hydrobromide and a crystalline form thereof. Compared to the known vortioxetine hydrobromide, the vortioxetine salts, solvates and crystalline forms of the present invention have improved features in stability, hygroscopicity and purity. The present invention also relates to preparation methods of the vortioxetine salts, solvates and crystalline forms, pharmaceutical compositions thereof and their uses in the manufacture of antidepressant drugs.

20 Claims, 6 Drawing Sheets

VORTIOXETINE SALT AND CRYSTAL THEREOF, THEIR PREPARATION METHOD, PHARMACEUTICAL COMPOSITIONS AND USAGE

CROSS-REFERENCE TO RELATED APPLICATIONS

This application claims priority as a continuation to International Application No. PCT/CN2014/079346, filed on Jun. 6, 2014 and entitled "VORTIOXETINE SALT AND CRYSTAL THEREOF, THEIR PREPARATION METHOD, PHARMACEUTICAL COMPOSITIONS AND USAGE," which in turn claims priority to Chinese application No. 201310415148.7 filed on Sep. 12, 2013, each of which is hereby incorporated by reference herein in its entirety.

FIELD OF THE INVENTION

The present invention relates to salts of antidepressant vortioxetine and crystalline forms thereof, and relates to preparation methods of the salts and crystalline forms thereof, pharmaceutical compositions thereof and their uses in preparing drugs for treating diseases including major depressive disorder, and methods for treating diseases including major depressive disorder as well.

BACKGROUND

Vortioxetine is a novel antidepressant developed by Tekeda Pharmaceuticals and H. Lundbeck A/S jointly, and used for the treatment of major depressive disorder. It is considered that the drug acts through a combination of two mechanisms: receptor activity modulation and reuptake inhibition. In vitro studies indicate vortioxetine is a 5-HT3 and 5-HT7 receptor antagonist, a 5-HT1B receptor partial agonist, a 5-HT1A receptor agonist and a 5-HT transporter inhibitor. In vivo nonclinical studies indicate vortioxetine can elevate levels of neurotransmitters (serotonin, noradrenaline, dopamine, acetyl choline and histamine) in specific cerebral regions. It is anticipated that the multimodal activity profile of vortioxetine may bring clinical benefits to patients with major depressive disorder whose disease cannot be adequately controlled by currently available drugs. The drug was approved by FDA in September 2013 for marketing under the trade name Brintellix. Its tablets contain vortioxetine hydrobromide as the active pharmaceutical ingredient, and the strengths are 5 mg, 10 mg, 15 mg and 20 mg.

The chemical name of vortioxetine hydrobromide is 1-[2-(2,4-dimethylphenylsulfanyl)phenyl]piperazine hydrobromide. Its English name is vortioxetine hydrobromide or LU AA21004. Its molecular formula is $C_{18}H_{22}N_2S \cdot HBr$. Its molecular weight is 379.36. Its chemical structural formula is shown below:

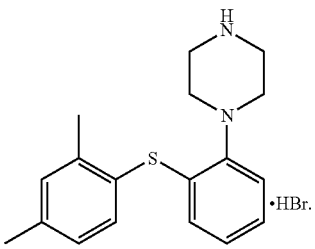 [SMILES: Cc1ccc(Sc2ccccc2N2CCNCC2)c(C)c1]

Patent document WO2003/029232A1 disclosed free base of vortioxetine and a preparation method thereof, also mentioned its solvates, isomers and pharmaceutically acceptable salts and uses in treating affective disorders. but did not provide preparation methods or characterization data of the above solvates, isomers or pharmaceutically acceptable salts of vortioxetine.

Patent documents WO2007/144005A1 and WO2008/113359A2 disclosed hydrobromide, hydrochloride, hydrochloride monohydrate, mesylate, fumarate, maleate, mesotartrate, L-(+)-tartrate, D-(−)-tartrate, sulfate, phosphate and nitrate of vortioxetine in their crystalline forms as well as preparation methods and characterization data thereof. Specifically, examples 4a to 4i in WO2007/144005A1 disclosed multiple crystalline forms of vortioxetine hydrobromide including a Form, β Form, γ Form, a hydrate solvate and an ethyl acetate solvate. Additionally, the patent document pointed out that, among the above disclosed crystalline forms, the β Form of vortioxetine hydrobromide is the most stable form and has high melting point, low solubility and good non-hygroscopicity, thus it is particularly suitable for preparing tablets.

In studies, the inventors of the present invention found out that the multiple crystalline forms of vortioxetine hydrobromide disclosed in WO2007/144005A1 have the following disadvantages:

The α Form of vortioxetine hydrobromide is unstable. It transformed to the β Form of vortioxetine hydrobromide at room temperature.

The β Form of vortioxetine hydrobromide failed to maintain its original crystalline form in the stability competition slurry test.

The γ Form of vortioxetine hydrobromide is very unstable and is hygroscopic. Its hygroscopicity under low-humidity conditions was 2.0%.

The hydrate of vortioxetine hydrobromide is unstable and is hygroscopic. It lost water under high-temperature conditions.

The ethyl acetate solvate of vortioxetine hydrobromide is unstable. It lost ethyl acetate under high-temperature conditions and transformed to hydrate under high-humidity conditions.

Patent documents WO2009/062517A1 and WO2012/025123A1 disclosed uses of vortioxetine hydrobromide in treating affective disorders such as depressions and anxiety disorders and in treating cognitive defects and pain. WO2012/025123A1 reported a method of treating central nervous system (CNS) diseases in long-term treatment patients by using vortioxetine hydrobromide.

In order to meet the strict requirements for the solid forms of active substances in solid pharmaceutical preparations and expand the selection options of the solid forms of active substances in formulation development, it is necessary to develop novel salts of vortioxetine and crystals or crystalline forms thereof in this field.

SUMMARY OF THE INVENTION

The first object of the present invention is to overcome the deficiency of the prior art, and to provide vortioxetine hemihydrobromide with better thermal stability and good non-hygroscopicity and a crystalline form thereof, and its preparation methods.

The second object of the present invention is to provide an isopropanol solvate of vortioxetine hydrobromide with higher purity and a crystalline form thereof, and its preparation methods.

The third object of the present invention is to provide a pharmaceutical composition comprising the above vortioxetine hemihydrobromide or the crystalline form thereof, or the above isopropanol solvate of vortioxetine hydrobromide or the crystalline form thereof.

The fourth object of the present invention is to provide pharmaceutical uses of the above vortioxetine hemihydrobromide or the crystalline form thereof, or the above isopropanol solvate of vortioxetine hydrobromide or the crystalline form thereof.

The fifth object of the present invention is to provide a method of treating diseases by using the above vortioxetine hemihydrobromide or the crystalline form thereof, the above isopropanol solvate of vortioxetine hydrobromide or the crystalline form thereof, or the above pharmaceutical composition.

The objects of the present invention are achieved by the following technical solutions:

A vortioxetine hemihydrobromide is provided, which is a compound formed from vortioxetine and hydrogen bromide at a molar ratio of 2:1. The structure formula is shown as formula (I):

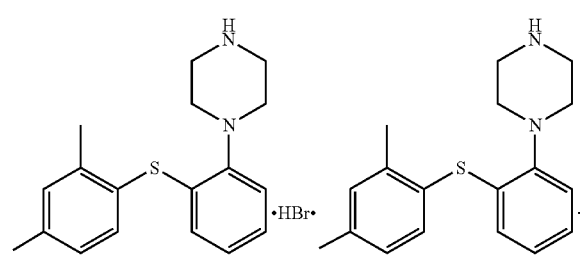

(I)

HPLC characterization indicates the vortioxetine hemihydrobromide is formed from vortioxetine and hydrogen bromide at a molar ratio of 2:1.

Childs et al reported cocrystal of polyamine hydrochloride and organic acid (benzoic acid, succinic acid and fumaric acid) may be formed by crystallization methods. The single crystal structure indicates, in the cocrystal structure, one chloride ion is simultaneously conjugated with two molecules (one polyamine molecule and one organic acid molecule) to form hydrogen bonds. Therefore, it is deduced that, in the vortioxetine hemihydrobromide of the present invention, bromide ion conjugates to two vortioxetine molecules in a similar way.

In addition, a preparation method of the vortioxetine hemihydrobromide is provided by the present invention, which comprises the following procedures: respectively prepare solutions of vortioxetine and hydrobromic acid in solvents, wherein the molar ratio of vortioxetine to hydrobromic acid is 10:1-2:1; mix the two solutions to produce a suspension and stir, then remove the solvents by rotary evaporation to obtain the vortioxetine hemihydrobromide.

Preferably, the solvents are selected from the group consisting of alcohols, esters, ketones and mixtures thereof.

More preferably, the solvents are selected from the group consisting of ethanol, isopropyl acetate and acetone.

Preferably, the temperature of the rotary evaporation is 10° C.-60° C.

Preferably, the concentration of vortioxetine in the solvent is 0.1-1 times of its solubility in the solvent at room temperature, more preferably 0.5-1 times; Preferably, the concentration of hydrobromic acid in the solvent is 0.5-1 times of its solubility in the solvent at room temperature.

Preferably, the method for forming the solution system of vortioxetine in the solvent comprises: add the solvent to vortioxetine or add vortioxetine to the solvent, and optionally produce the solution by stirring and/or sonication.

Preferably, the method for forming the solution system of hydrobromic acid in the solvent comprises: mix well hydrobromic acid and the solvent, and optionally stirring and/or sonication is conducted.

The solvent used for forming the solution system of vortioxetine and that used for forming the solution system of hydrobromic acid may be the same or be different; preferably, the same solvent is used.

Furthermore, the present invention provides a crystalline form of vortioxetine hemihydrobromide (hereinafter referred to as "vortioxetine hemihydrobromide crystal"). Measured with Cu-Kα radiation, the X-ray powder diffraction pattern of the crystalline form of vortioxetine hemihydrobromide, expressed as 2θ angles, has the following characteristic peaks: 4.3±0.2°, 14.9±0.2°, 17.8±0.2°, 18.9±0.2°, 19.4±0.2° and 22.8±0.2°.

More preferably, the X-ray powder diffraction pattern of the crystalline form of vortioxetine hemihydrobromide, expressed as 2θ angles, has the following characteristic peaks: 4.3±0.2°, 14.9±0.2°, 17.1±0.2°, 17.8±0.2°, 18.9±0.2°, 19.4±0.2°, 22.0±0.2°, 22.4±0.2°, 22.8±0.2°, 24.4±0.2°, 25.4±0.2° and 29.7±0.2°.

Further preferably, the X-ray powder diffraction pattern of the crystalline form of vortioxetine hemihydrobromide, expressed as 2θ angles, has the following characteristic peaks with the following relative intensities:

| Diffraction angle 2θ | Relative intensity % |
| --- | --- |
| 4.3 ± 0.2° | 25.6 |
| 14.9 ± 0.2° | 23.3 |
| 16.8 ± 0.2° | 11.2 |
| 17.1 ± 0.2° | 17.6 |
| 17.8 ± 0.2° | 100.0 |
| 18.9 ± 0.2° | 22.5 |
| 19.4 ± 0.2° | 49.5 |
| 22.0 ± 0.2° | 24.5 |
| 22.4 ± 0.2° | 16.7 |
| 22.8 ± 0.2° | 31.8 |
| 24.4 ± 0.2° | 17.7 |
| 25.4 ± 0.2° | 15.6 |
| 25.9 ± 0.2° | 10.1 |
| 27.8 ± 0.2° | 11.8 |
| 28.6 ± 0.2° | 11.1 |
| 29.0 ± 0.2° | 10.3 |
| 29.7 ± 0.2° | 24.0 |
| 31.3 ± 0.2° | 12.9 |

Non-restrictively, in one specific embodiment, the XRPD pattern of the crystalline form of vortioxetine hemihydrobromide is shown in FIG. 2.

The crystalline form of vortioxetine hemihydrobromide is an anhydrous form; its melting point is about 213° C.; its decomposition temperature is about 216° C.

The Fourier infrared spectrum of the crystalline form of vortioxetine hemihydrobromide has characteristic peaks at the wave numbers of 3171, 2952, 2916, 2828, 2808, 2733, 1580, 1474, 1439, 1146, 1053, 924, 861 and 735 cm$^{-1}$.

The vortioxetine hemihydrobromide and the crystalline form thereof in the present invention have the following advantages:

① In the stability competition test, when slurried in water or ethanol, the most stable crystalline form reported in patent document WO2007/144005A1 (i.e. the β Form of vortioxetine hydrobromide) failed to maintain its original crystalline form and transformed to the vortioxetine hemihydrobromide crystalline form of the present invention, indicating the vortioxetine hemihydrobromide crystalline form of the present invention has better stability in water and in ethanol. This property suggests the vortioxetine hemihydrobromide crystalline form of the present invention is a more suitable form for wet granulation processes of solid formulations or preparation of oral suspensions, allowing satisfactory stability in pharmaceutical manufacturing and/or storage.

② In the hygroscopicity comparison test, the vortioxetine hemihydrobromide crystalline form of the present invention is less hygroscopic than the known β Form of vortioxetine hydrobromide, indicating the vortioxetine hemihydrobromide crystalline form of the present invention is less hygroscopic. It is more humidity robust and thus less likely to have content uniformity and stability issues induced by environment during pharmaceutical production and storage, thus reduce the risk of inefficacy and safety issue caused thereby and improve dosing accuracy.

③ Compared to the known vortioxetine hydrobromide, the vortioxetine hemihydrobromide of the present invention, with only 0.5 hydrogen bromide molecule, has a relatively lower toxicity level and a higher active ingredient content. It is, therefore, safer and more effective in formulations and more suitable for high-dose clinical use.

④ Compared to the known vortioxetine hydrobromide, the vortioxetine hemihydrobromide of the present invention could be more suitable for sustained-release formulation preparations.

Furthermore, the present invention provides a preparation method of the crystalline form of vortioxetine hemihydrobromide, which comprises the following procedures: respectively prepare solution systems of vortioxetine and hydrobromic acid in solvents, wherein the solvents are selected from the group consisting of $C_1$-$C_4$ alcohols, $C_4$-$C_5$ esters, $C_3$-$C_4$ ketones and mixtures thereof, the molar ratio of vortioxetine to hydrobromic acid in the two solution systems is 10:1-2:1; mix the two solution systems to produce a suspension and stir to crystallize for 1-48 hours at a crystallization temperature of −10-50° C., then remove the solvent to obtain the crystalline form of vortioxetine hemihydrobromide.

Preferably, the solvents are selected from the group consisting of ethanol, isopropanol, ethyl acetate and acetone.

Preferably, the molar ratio of vortioxetine to hydrobromic acid is 4:1-2:1.

Preferably, the crystallization temperature is room temperature, and the duration of crystallization is 2-4 h.

Preferably, the concentration of vortioxetine in the solvent is 0.1-1 times of its solubility in the solvent at the crystallization temperature, more preferably 0.5-1 times; Preferably, the concentration of hydrobromic acid in the solvent is 0.5-1 times of its solubility in the solvent at the crystallization temperature.

More preferably, when the solvent is ethanol, the concentration of vortioxetine in ethanol at room temperature is 7-67 mg/mL, most preferably 54-67 mg/mL.

Preferably, the method for forming the solution system of vortioxetine in the solvent comprises: add the solvent to vortioxetine or add vortioxetine to the solvent to produce the solution system, optionally by stirring and/or sonication.

Preferably, the method for forming the solution system of hydrobromic acid in the solvent comprises: mix hydrobromic acid and the solvent well to produce the solution system by stirring and/or sonication.

The solvent used for forming the solution system of vortioxetine and that used for forming the solution system of hydrobromic acid may be the same or be different; preferably, the same solvent is used.

According to the objects of the present invention, the present invention provides an isopropanol solvate of vortioxetine hydrobromide, with every molecule of the vortioxetine hydrobromide isopropanol solvate containing about one molecule of isopropanol. The structural formula is shown as formula (II):

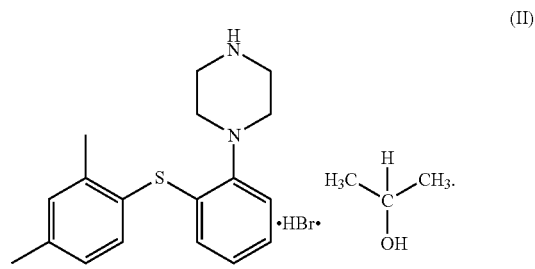

According to the TGA thermogram of the vortioxetine hydrobromide isopropanol solvate, a weight loss of about 13.6% occurs before 150° C., indicating every molecule of the vortioxetine hydrobromide isopropanol solvate contains about one molecule of isopropanol.

Additionally, a preparation method of the vortioxetine hydrobromide isopropanol solvate is provided by the present invention, which comprises the following procedures: prepare solution systems of vortioxetine and hydrobromic acid in solvents respectively, wherein the solvents are selected from isopropanol or aqueous solution of isopropanol, the molar ratio of vortioxetine to hydrobromic acid in the two solution systems is 1:1-1:2 and the combined total mole quantities of isopropanol are not less than that of vortioxetine; mix the two solution systems to produce a suspension and stir; remove the solvents to obtain the vortioxetine hydrobromide isopropanol solvate.

Preferably, the volume ratio of isopropanol to water in the aqueous solution of isopropanol is 5:1-2:1.

Preferably, the solvents are removed by rotary evaporation method and the rotary evaporation takes place at a temperature selected from 10° C. to 50° C.

Preferably, the concentration of vortioxetine in the solution system is 0.1-1 times of its solubility in the solvent at room temperature, more preferably 0.5-1 times.

Preferably, the concentration of hydrobromic acid in the solution system is 0.5-1 times of its solubility in the solvent at room temperature.

Preferably, the method for forming the solution system of vortioxetine in the solvent comprises: add the solvent to vortioxetine or add vortioxetine to the solvent to produce the solution system, optionally by stirring and/or sonication.

Preferably, the method for forming the solution system of hydrobromic acid in the solvent comprises: mix well hydrobromic acid and the solvent to produce the solution system, optionally by stirring and/or sonication.

Furthermore, the present invention provides a crystalline form of the vortioxetine hydrobromide isopropanol solvate. Measured with Cu-Kα radiation, the X-ray powder diffraction pattern of the crystalline form of the vortioxetine hydrobromide isopropanol solvate, expressed as 2θ angles, has the following characteristic peaks: 6.5±0.2°, 10.4±0.2°, 12.6±0.2°, 17.8±0.2°, 19.0±0.2° and 19.4±0.2°.

More preferably, the X-ray powder diffraction pattern of the crystalline form of the vortioxetine hydrobromide isopropanol solvate, expressed as 2θ angles, has the following characteristic peaks:

6.5±0.2°, 8.1±0.2°±0.2°, 10.4±0.2°, 12.6±0.2°, 17.8±0.2°, 19.0±0.2°, 19.4±0.2°, 20.3±0.2°, 20.8±0.2°, 23.7±0.2°, 24.3±0.2° and 28.0±0.2°.

Further preferably, the X-ray powder diffraction pattern of the crystalline form of the vortioxetine hydrobromide isopropanol solvate, expressed as 2θ angles, has the following characteristic peaks with the following relative intensities:

| Diffraction angle 2θ | Relative intensity % |
| --- | --- |
| 6.5 ± 0.2° | 55.7 |
| 8.1 ± 0.2° | 19.6 |
| 10.4 ± 0.2° | 31.9 |
| 12.6 ± 0.2° | 27.6 |
| 17.1 ± 0.2° | 14.3 |
| 17.8 ± 0.2° | 29.5 |
| 19.0 ± 0.2° | 100.0 |
| 19.4 ± 0.2° | 57.5 |
| 20.3 ± 0.2° | 21.3 |
| 20.8 ± 0.2° | 30.2 |
| 23.0 ± 0.2° | 21.6 |
| 23.7 ± 0.2° | 47.1 |
| 24.3 ± 0.2° | 26.4 |
| 25.7 ± 0.2° | 26.9 |
| 26.4 ± 0.2° | 22.0 |
| 28.0 ± 0.2° | 35.3 |
| 28.6 ± 0.2° | 19.9 |

Non-restrictively, in one specific embodiment, the XRPD pattern of the crystalline form of the vortioxetine hydrobromide isopropanol solvate is shown in FIG. 8.

The Fourier infrared spectrum of the crystalline form of the vortioxetine hydrobromide isopropanol solvate has characteristic peaks at the wave numbers of 3295, 2967, 2813, 2716, 2520, 1615, 1473, 1378, 1229, 1126, 1045, 948, 832, 762 and 730 cm$^{-1}$.

Furthermore, the present invention provides a preparation method of the crystalline form of the vortioxetine hydrobromide isopropanol solvate, which is either of the following preparation methods:

1) At 40-70° C., prepare solution systems of vortioxetine and hydrobromic acid in solvents respectively, wherein the solvents are selected from isopropanol or aqueous solution of isopropanol, the molar ratio of vortioxetine to hydrobromic acid in the two solution systems is 1:1-1:2 and the combined total mole quantities of isopropanol are not less than that of vortioxetine; mix the two solution systems and stir for 10-30 minutes to produce a suspension; then stir the suspension at room temperature for 1-48 hours to crystalliza, and remove the solvents to obtain the crystalline form of the vortioxetine hydrobromide isopropanol solvate.

Preferably, the molar ratio of vortioxetine to hydrobromic acid is 1:1-1:1.5.

Preferably, the volume ratio of isopropanol to water in the aqueous solution of isopropanol is 5:1-2:1.

Preferably, the duration of crystallization is 1-10 hours.

Preferably, the concentration of vortioxetine in the solution system is 0.1-1 times of its solubility in the solvent at 40-70° C., more preferably 0.5-1 times.

Preferably, the concentration of hydrobromic acid in the solution system is 0.5-1 times of its solubility in the solvent at 40-70° C.

Preferably, the method for forming the solution system of vortioxetine in the solvent comprises: add the solvent to vortioxetine or add vortioxetine to the solvent to produce the solution system, optionally by stirring and/or sonication.

Preferably, the method for forming the solution system of hydrobromic acid in the solvent comprises: mix hydrobromic acid and the solvent well to produce the solution system, optionally by stirring and/or sonication.

The solvent used for forming the solution system of vortioxetine and that used for forming the solution system of hydrobromic acid may be the same or be different; preferably, the same solvent is used.

2) Form a suspension of vortioxetine hydrobromide in isopropanol or aqueous solution of isopropanol, wherein the mole quantities of isopropanol is not less than that of vortioxetine; stir for crystallization, and remove the solvent(s) to obtain the crystalline form of the vortioxetine hydrobromide isopropanol solvate.

Preferably, the volume ratio of isopropanol to water in the aqueous solution of isopropanol is 5:1-2:1, more preferably 5:1-3:1.

Preferably, the crystallization temperature is 10-50° C., more preferably room temperature.

Preferably, the duration of crystallization is 10-48 h, more preferably 10-24 h.

Preferably, the amount of vortioxetine hydrobromide in the suspension is 2-10 times of its solubility in isopropanol or aqueous solution of isopropanol, more preferably 2-5 times.

The vortioxetine hydrobromide isopropanol solvate and the crystal thereof in the present invention have the following advantages and application properties:

① According to the HPLC purity analysis, compared to the known vortioxetine hydrobromide, the vortioxetine hydrobromide isopropanol solvate of the present invention has a higher purity value, and the vortioxetine hydrobromide obtained by desolvation of the vortioxetine hydrobromide isopropanol solvate of the present invention also has a higher purity value, indicating the vortioxetine hydrobromide isopropanol solvate formation is good for purification of vortioxetine hydrobromide.

② When placed in desiccators maintained at 10% RH-90% RH at room temperature for 4 months, the crystalline form of the vortioxetine hydrobromide isopropanol solvate of the present invention remained unchanged. The result suggests the crystalline form of the isopropanol solvate of vortioxetine hydrobromide isopropanol solvate of the present invention has good stability. It is more temperature and humidity robust and is less likely to have content uniformity and stability issues during pharmaceutical production and storage, thus reduces the risk of inefficacy and safety issue caused thereby and improves dosing accuracy.

The hydrobromic acid used in the present invention is an aqueous solution of hydrogen bromide, which is commercially purchased and has a concentration of 40% (w/w).

In studies, the inventors of the present invention also developed vortioxetine besylate, vortioxetine citrate, vortioxetine succinate, vortioxetine p-toluenesulfonate, vortioxetine p-chlorobenzenesulfonate, vortioxetine ethanedisulfonate, vortioxetine α-ketoglutarate, vortioxetine 1,5-naphthalenedisulfonate, vortioxetine 2-naphthalenesulfonate, vortioxetine 3-hydroxy-2-naphthoate, vortioxetine 1-hydroxy-2-naphthoate, vortioxetine oxalate and their crystalline forms, and preparation methods thereof.

Compared to the known vortioxetine salts or crystalline forms thereof, the above vortioxetine besylate, vortioxetine citrate, vortioxetine succinate, vortioxetine p-toluenesulfonate, vortioxetine p-chlorobenzenesulfonate, vortioxetine ethanedisulfonate, vortioxetine α-ketoglutarate, vortioxetine 1,5-naphthalenedisulfonate, vortioxetine 2-naphthalenesulfonate, vortioxetine 3-hydroxy-2-naphthoate, vortioxetine 1-hydroxy-2-naphthoate, vortioxetine oxalate and crystalline forms thereof have one or more improved features, e.g. higher crystallinity, higher solubility, higher dissolution rates, better crystal morphology, greater thermal stability and storage stability, lower hygroscopicity, better flowability and better processing properties.

A preparation method of the vortioxetine besylate, comprises the following procedures: prepare solution systems of vortioxetine and benzenesulfonic acid in soluble solvents respectively, wherein the molar ratio of vortioxetine to benzenesulfonic acid is 1:1-1:2; mix the two systems to produce a suspension for reaction; after completion of the reaction, remove the solvents to obtain the vortioxetine besylate. Preferably, the soluble solvents are selected from the group consisting of alcohols, esters, ketones, alkanes and mixtures thereof.

Furthermore, the present invention provides crystalline form B of vortioxetine besylate, measured with Cu-Kα radiation, the X-ray powder diffraction pattern of the crystalline form B of vortioxetine besylate has characteristic peaks at 2θ angles of 7.9±0.2°, 15.7±0.2°, 16.2±0.2°, 17.7±0.2°, 19.6±0.2° and 23.6±0.2°.

The present invention also provides a preparation method of the crystalline form B of vortioxetine besylate, which comprises the following procedures: prepare solution systems of vortioxetine and benzenesulfonic acid in soluble solvents respectively, wherein the soluble solvents are selected from the group consisting of $C_1$-$C_4$ alcohols, $C_4$-$C_5$ esters, $C_3$-$C_4$ ketones, n-heptane and mixtures thereof and the molar ratio of vortioxetine to benzenesulfonic acid is 1:1-1:2; mix the two systems to produce a suspension; stir the suspension for 1-48 h at −10° C.-50° C.; then remove the solvents to obtain the crystalline form B.

A preparation method of the vortioxetine citrate comprises the following procedures: prepare solution systems of vortioxetine and citric acid in soluble solvents respectively, wherein the molar ratio of vortioxetine to citric acid is 1:1-1:2; mix the two systems to produce a suspension for reaction; after completion of the reaction, remove the solvents to obtain the vortioxetine citrate. Preferably, the soluble solvents are selected from the group consisting of alcohols, esters, ketones and mixtures thereof.

Furthermore, the present invention provides crystalline form C of vortioxetine citrate, measured with Cu-Kα radiation, the X-ray powder diffraction pattern of the crystalline form C of vortioxetine citrate has characteristic peaks at 2θ angles of 5.1±0.2°, 13.7±0.2°, 15.6±0.2°, 16.4±0.2°, 17.6±0.2° and 20.2±0.2°.

The present invention also provides a preparation method of the crystalline form C of vortioxetine citrate, which comprises the following procedures: prepare solution systems of vortioxetine and citric acid in soluble solvents respectively, wherein the soluble solvents are selected from the group consisting of $C_1$-$C_4$ alcohols, $C_4$-$C_5$ esters, $C_3$-$C_4$ ketones and mixtures thereof and the molar ratio of vortioxetine to citric acid is 1:1-1:2; mix the two systems to produce a suspension; stir the suspension for 1-48 h at −10° C.-50° C.; then remove the solvent to obtain the crystalline form C.

A preparation method of the vortioxetine succinate comprises the following procedures: prepare solution systems of vortioxetine and succinic acid in soluble solvents respectively, wherein the molar ratio of vortioxetine to succinic acid is 1:1-1:2; mix the two systems to produce a suspension for reaction; after completion of the reaction, remove the solvent to obtain the vortioxetine succinate. Preferably, the soluble solvents are selected from the group consisting of alcohols, esters, ketones, ethers, alkanes and mixtures thereof.

Furthermore, the present invention provides the crystalline form S of vortioxetine succinate, measured with Cu-Kα radiation, the X-ray powder diffraction pattern of the crystalline form S of vortioxetine succinate has characteristic peaks at 2θ angles of 5.0±0.2°, 11.4±0.2°, 13.5±0.2°, 18.2±0.2°, 20.7±0.2° and 27.2±0.2°.

The present invention also provides a preparation method of the crystalline form S of vortioxetine succinate, which comprises the following procedures: prepare solution systems of vortioxetine and succinic acid in soluble solvents respectively, wherein the soluble solvents are selected from the group consisting of $C_1$-$C_4$ alcohols, $C_4$-$C_5$ esters, $C_3$-$C_4$ ketones, methyl tert-butyl ether, n-heptane and mixtures thereof and the molar ratio of vortioxetine to succinic acid is 1:1-1:2; mixing the two systems to produce a suspension; stir the suspension for 1-48 h at −10° C.-50° C.; then remove the solvents to obtain the crystalline form S.

A preparation method of the vortioxetine p-toluenesulfonate comprises the following procedures: prepare solution systems of vortioxetine and p-toluenesulfonic acid in soluble solvents respectively, wherein the molar ratio of vortioxetine to p-toluenesulfonic acid is 1:1-1:2; mix the two systems to produce a suspension for reaction; after completion of the reaction, remove the solvents to obtain the vortioxetine p-toluenesulfonate. Preferably, the soluble solvents are selected from the group consisting of alcohols, esters, ketones, ethers and mixtures thereof.

Furthermore, the present invention provides crystalline form T of vortioxetine p-toluenesulfonate, measured with Cu-Kα radiation, the X-ray powder diffraction pattern of the crystalline form T of vortioxetine p-toluenesulfonate has characteristic peaks at 2θ angles of 8.0±0.2°, 15.8±0.2°, 16.1±0.2°, 17.6±0.2°, 20.0±0.2° and 20.8±0.2°.

The present invention also provides a preparation method of the crystalline form T of vortioxetine p-toluenesulfonate, which comprises the following procedures: prepare solution systems of vortioxetine and p-toluenesulfonic acid in soluble solvents respectively, wherein the soluble solvents are selected from the group consisting of $C_1$-$C_4$ alcohols, $C_4$-$C_5$ esters, $C_3$-$C_4$ ketones, methyl tert-butyl ether and mixtures thereof and the molar ratio of vortioxetine to p-toluenesulfonic acid is 1:1-1:2; mix the two systems to produce a suspension; stir the suspension for 1-48 h at −10° C.-50° C.; then remove the solvents to obtain the crystalline form T.

A preparation method of the vortioxetine p-chlorobenzenesulfonate comprises the following procedures: prepare solution systems of vortioxetine and p-chlorobenzenesulfonic acid in soluble solvents respectively, wherein the molar ratio of vortioxetine to p-chlorobenzenesulfonic acid is 1:1-1:2; mix the two systems to produce a suspension for reaction; after completion of the reaction, remove the solvent to obtain the vortioxetine p-chlorobenzenesulfonate. Preferably, the soluble solvents are selected from the group consisting of alcohols, esters, ketones and mixtures thereof.

Furthermore, the present invention provides crystalline form Ch of vortioxetine p-chlorobenzenesulfonate, measured with Cu-Kα radiation, the X-ray powder diffraction pattern of the crystalline form Ch of vortioxetine p-chlorobenzenesulfonate has characteristic peaks at 2θ angles of 15.7±0.2°, 16.2±0.2°, 17.7±0.2°, 20.0±0.2°, 22.7±0.2° and 23.1±0.2°.

The present invention also provides a preparation method of the crystalline form Ch of vortioxetine p-chlorobenzenesulfonate, which comprises the following procedures: prepare solution systems of vortioxetine and p-chlorobenzenesulfonic acid in soluble solvents respectively, wherein the soluble solvents are selected from the group consisting of $C_1$-$C_4$ alcohols, $C_4$-$C_5$ esters, $C_3$-$C_4$ ketones and mixtures thereof and the molar ratio of vortioxetine to p-chlorobenzenesulfonic acid is 1:1-1:2; mix the two systems to produce a suspension; stir the suspension for 1-48 h at −10° C.-50° C.; then remove the solvents to obtain the crystalline form Ch.

A preparation method of the vortioxetine ethanedisulfonate comprises the following procedures: prepare solution systems of vortioxetine and ethanedisulfonic acid in soluble solvents respectively, wherein the molar ratio of vortioxetine to ethanedisulfonic acid is 1:1-1:2; mix the two systems to produce a suspension for reaction; after completion of the reaction, remove the solvents to obtain the vortioxetine ethanedisulfonate. Preferably, the soluble solvents are selected from the group consisting of alcohols, esters, ketones and mixtures thereof.

Furthermore, the present invention provides crystalline form E of vortioxetine ethanedisulfonate, measured with Cu-Kα radiation, the X-ray powder diffraction pattern of the crystalline form E of vortioxetine ethanedisulfonate has characteristic peaks at 2θ angles of 3.7±0.2°, 4.4±0.2°, 16.9±0.2°, 18.7±0.2°, 19.7±0.2° and 20.4±0.2°.

The present invention also provides a preparation method of the crystalline form E of vortioxetine ethanedisulfonate, which comprises the following procedures: prepare solution systems of vortioxetine and ethanedisulfonic acid in soluble solvents respectively, wherein the soluble solvents are selected from the group consisting of $C_1$-$C_4$ alcohols, $C_4$-$C_5$ esters, $C_3$-$C_4$ ketones and mixtures thereof and the molar ratio of vortioxetine to ethanedisulfonic acid is 1:1-1:2; mix the two systems to produce a suspension; stir the suspension for 1-48 h at −10° C.-50° C.; then remove the solvents to obtain the crystalline form E.

A preparation method of the vortioxetine α-ketoglutarate comprises the following procedures: prepare solution systems of vortioxetine and α-ketoglutaric acid in soluble solvents respectively, wherein the molar ratio of vortioxetine to α-ketoglutaric acid is 1:1-1:2; mix the two systems to produce a suspension for reaction; after completion of the reaction, remove the solvents to obtain the vortioxetine α-ketoglutarate. Preferably, the soluble solvents are selected from the group consisting of alcohols, esters, ketones, ethers, alkanes and mixtures thereof.

Furthermore, the present invention provides the crystalline form G of vortioxetine α-ketoglutarate, measured with Cu-Kα radiation, the X-ray powder diffraction pattern of the crystalline form G of vortioxetine α-ketoglutarate has characteristic peaks at 2θ angles of 4.4±0.2°, 11.3±0.2°, 12.8±0.2°, 16.5±0.2°, 20.8±0.2° and 21.4±0.2°.

The present invention also provides a preparation method of the crystalline form G of vortioxetine α-ketoglutarate, which comprises the following procedures: prepare solution systems of vortioxetine and α-ketoglutaric acid in soluble solvents respectively, wherein the soluble solvents are selected from the group consisting of $C_1$-$C_4$ alcohols, $C_4$-$C_5$ esters, $C_3$-$C_4$ ketones, methyl tert-butyl ether, n-heptane and mixtures thereof and the molar ratio of vortioxetine to α-ketoglutaric acid is 1:1-1:2; mix the two systems to produce a suspension; stir the suspension for 1-48 h at −10° C.-50° C.; then remove the solvents to obtain the crystalline form G.

A preparation method of the vortioxetine 1,5-naphthalenedisulfonate comprises the following procedures: prepare solution systems of vortioxetine and 1,5-naphthalene disulfonic acid in soluble solvents respectively, wherein the molar ratio of vortioxetine to 1,5-naphthalene disulfonic acid is 1:1-1:2; mix the two systems to produce a suspension for reaction; after completion of the reaction, remove the solvents to obtain the vortioxetine 1,5-naphthalenedisulfonate. Preferably, the soluble solvents are selected from the group consisting of alcohols, esters, ketones, alkanes and mixtures thereof.

Furthermore, the present invention provides the crystalline form N of vortioxetine 1,5-naphthalenedisulfonate, measured with Cu-Kα radiation, the X-ray powder diffraction pattern of the crystalline form N of vortioxetine 1,5-napadisilate has characteristic peaks at 2θ angles of 13.1±0.2°, 14.4±0.2°, 15.9±0.2°, 18.0±0.2°, 18.9±0.2° and 23.4±0.2°.

The present invention also provides a preparation method of the crystalline form N of vortioxetine 1,5-naphthalenedisulfonate, which comprises the following procedures: prepare solution systems of vortioxetine and 1,5-naphthalene disulfonic acid in soluble solvents respectively, wherein the soluble solvents are selected from the group consisting of $C_1$-$C_4$ alcohols, $C_4$-$C_5$ esters, $C_3$-$C_4$ ketones, n-heptane and mixtures thereof and the molar ratio of vortioxetine to 1,5-naphthalene disulfonic acid is 1:1-1:2; mix the two systems to produce a suspension; stir the suspension for 1-48 h at −10° C.-50° C.; then remove the solvents to obtain the crystalline form N.

A preparation method of the vortioxetine 2-naphthalenesulfonate comprises the following procedures: prepare solution systems of vortioxetine and 2-naphthalene sulfonic acid in soluble solvents respectively, wherein the molar ratio of vortioxetine to 2-naphthalene sulfonic acid is 1:1-1:2; mix the two systems to produce a suspension for reaction; after completion of the reaction, remove the solvents to obtain the vortioxetine 2-naphthalenesulfonate. Preferably, the soluble solvents are selected from the group consisting of alcohols, esters, ketones, ethers and mixtures thereof.

Furthermore, the present invention provides the crystalline form Na of vortioxetine 2-naphthalenesulfonate, measured with Cu-Kα radiation, the X-ray powder diffraction pattern of the crystalline form Na of vortioxetine 2-naphthalenesulfonate has characteristic peaks at 2θ angles of 6.4±0.2°, 12.7±0.2°, 18.6±0.2°, 19.7±0.2°, 20.0±0.2° and 24.4±0.2°.

The present invention also provides a preparation method of the crystalline form Na of vortioxetine 2-naphthalenesulfonate, which comprises the following procedures: prepare solution systems of vortioxetine and 2-naphthalene sulfonic acid in soluble solvents respectively, wherein the soluble solvents are selected from the group consisting of $C_1$-$C_4$ alcohols, $C_4$-$C_5$ esters, $C_3$-$C_4$ ketones, methyl tert-butyl ether and mixtures thereof and the molar ratio of vortioxetine to 2-naphthalene sulfonic acid is 1:1-1:2; mix the two systems to produce a suspension; stir the suspension for 1-48 h at −10° C.-50° C.; then remove the solvents to obtain the crystalline form Na.

A preparation method of the vortioxetine 3-hydroxy-2-naphthoate comprises the following procedures: prepare solution systems of vortioxetine and 3-hydroxy-2-naphthoic acid in soluble solvents respectively, wherein the molar ratio of vortioxetine to 3-hydroxy-2-naphthoic acid is 1:1-1:2; mix the two systems to produce a suspension for reaction; after completion of the reaction, remove the solvents to obtain the vortioxetine 3-hydroxy-2-naphthoate. Preferably, the soluble solvents are selected from the group consisting of alcohols, esters, ketones, ethers, alkanes and mixtures thereof.

Furthermore, the present invention provides the crystalline form H of vortioxetine 3-hydroxy-2-naphthoate, measured with Cu-Kα radiation, the X-ray powder diffraction pattern of the crystalline form H of vortioxetine 3-hydroxy-2-naphthoate has characteristic peaks at 2θ angles of 11.8±0.2°, 15.2±0.2°, 16.9±0.2°, 17.8±0.2°, 18.5±0.2° and 21.4±0.2°.

The present invention also provides a preparation method of the crystalline form H of vortioxetine 3-hydroxy-2-naphthoate, which comprises the following procedures: prepare solution systems of vortioxetine and 3-hydroxy-2-naphthoic acid in soluble solvents respectively, wherein the soluble solvents are selected from the group consisting of $C_1$-$C_4$ alcohols, $C_4$-$C_5$ esters, $C_3$-$C_4$ ketones, methyl tert-butyl ether, n-heptane and mixtures thereof and the molar ratio of vortioxetine to 3-hydroxy-2-naphthoic acid is 1:1-1:2; mix the two systems to produce a suspension; stir the suspension for 1-48 h at −10° C.-50° C.; then remove the solvents to obtain the crystalline form H.

A preparation method of the vortioxetine 1-hydroxy-2-naphthoate comprises the following procedures: prepare solution systems of vortioxetine and 1-hydroxy-2-naphthoic acid in soluble solvents respectively, wherein the molar ratio of vortioxetine to 1-hydroxy-2-naphthoic acid is 1:1-1:2; mix the two systems to produce a suspension for reaction; after completion of the reaction, remove the solvents to obtain the vortioxetine 1-hydroxy-2-naphthoate. Preferably, the soluble solvents are selected from the group consisting of alcohols, esters, ketones, ethers, alkanes and mixtures thereof.

Furthermore, the present invention provides the crystalline form Hy of vortioxetine 1-hydroxy-2-naphthoate, measured with Cu-Kα radiation, the X-ray powder diffraction pattern of the crystalline form Hy of vortioxetine 1-hydroxy-2-naphthoate has characteristic peaks at 2θ angles of 6.1±0.2°, 7.2±0.2°, 11.2±0.2°, 14.3±0.2°, 18.9±0.2° and 22.4±0.2°.

The present invention also provides a preparation method of the crystalline form Hy of vortioxetine 1-hydroxy-2-naphthoate, which comprises the following procedures: prepare solution systems of vortioxetine and 1-hydroxy-2-naphthoic acid in soluble solvents respectively, wherein the soluble solvents are selected from the group consisting of $C_1$-$C_4$ alcohols, $C_4$-$C_5$ esters, $C_3$-$C_4$ ketones, methyl tert-butyl ether, n-heptane and mixtures thereof and the molar ratio of vortioxetine to 1-hydroxy-2-naphthoic acid is 1:1-1:2; mix the two systems to produce a suspension; stir the suspension for 1-48 h at −10° C.-50° C.; then remove the solvents to obtain the crystalline form Hy.

A preparation method of the vortioxetine oxalate comprises the following procedures: prepare solution systems of vortioxetine and oxalic acid in soluble solvents respectively, wherein the molar ratio of vortioxetine to oxalic acid is 1:1-1:2; mix the two systems to produce a suspension for reaction; after completion of the reaction, remove the solvents to obtain the vortioxetine oxalate. Preferably, the soluble solvents are selected from the group consisting of alcohols, esters, ketones, ethers and mixtures thereof.

Furthermore, the present invention provides the crystalline form O of vortioxetine oxalate, measured with Cu-Kα radiation, the X-ray powder diffraction pattern of the crystalline form O of vortioxetine oxalate has characteristic peaks at 2θ angles of 3.6±0.2°, 10.4±0.2°, 11.9±0.2°, 14.7±0.2°, 19.2±0.2° and 20.7±0.2°.

The present invention also provides a preparation method of the crystalline form O of vortioxetine oxalate, which comprises the following procedures: prepare solution systems of vortioxetine and oxalic acid in soluble solvents respectively, wherein the soluble solvents are selected from the group consisting of $C_1$-$C_4$ alcohols, $C_4$-$C_5$ esters, $C_3$-$C_4$ ketones, methyl tert-butyl ether and mixtures thereof and the molar ratio of vortioxetine to oxalic acid is 1:1-1:2; mix the two systems to produce a suspension; stir the suspension for 1-48 h at −10° C.-50° C.; then remove the solvents to obtain the crystalline form O.

In the above preparation methods of the present invention:

The "stir" may be performed by routine methods in the field. For example, stirring methods include magnetic stirring and mechanical stirring. The stirring speed is 50~1800 r/min, preferably 300~900 r/min.

The "remove the solvents" may be performed by routine techniques in the field, e.g. filtration, centrifugation, rotary evaporation, and evaporation, etc. The "filtration" usually refers to suction filtration at room temperature under a pressure less than the atmospheric pressure, which is preferably lower than 0.09 MPa. The detailed operation of "centrifugation" is: place the sample to be separated in a 2 mL centrifuge tube, rotate at 6000 r/min until the solid completely settles at the bottom of the tube. The "rotary evaporation method" usually refers to rotary evaporation at 10-60° C. under a pressure less than the atmospheric pressure, which is preferably lower than 0.09 MPa.

Optionally, the salts and solvates of vortioxetine or crystalline forms thereof prepared by the above methods can be washed by routine methods in the field. Washing solvent is preferably the solvent used in the solution systems in the preparation method. Depending on samples' situations, amount and frequency of the washing solvent may be adjusted.

The salts and solvates of vortioxetine or crystals or crystalline forms thereof prepared by the above methods can be dried by routine methods in the field. Drying conditions include normal-temperature drying, drying under reduced pressure and blast drying. Drying device may be a fume hood, a blast oven or a vacuum oven. The drying temperature is 10-60° C., preferably 10-40° C.; the duration of drying is 10-72 h, preferably 10-48 h and more preferably 10-24 h. Drying under reduced pressure is preferably used, and the pressure is preferably less than 0.09 MPa.

Crystalline forms of the present invention are pure and basically free of any other crystalline forms. For example, the crystalline form of vortioxetine hemihydrobromide of the present invention is free of the known crystalline forms of vortioxetine hydrobromide, or the crystalline form of the vortioxetine hydrobromide isopropanol solvate of the present invention is free of the known crystalline forms of vortioxetine hydrobromide, wherein examples of the known crystalline forms of vortioxetine hydrobromide include the α Form, the β Form, the γ Form, the hydrate or the ethyl acetate solvate. In the present invention, when "basically free of" is used for describing a novel crystalline form, it means that the content of other crystalline forms in the novel crystalline form is less than 20% (w/w), specifically less than 10% (w/w), more specifically less than 5% (w/w) and further more specifically less than 1% (w/w). X-ray powder diffraction was used to perform the phase purity analysis of the solids obtained from the present invention.

In the present invention, "crystals" or "crystalline forms" refer to those characterized by X-ray powder diffraction patterns. Crystals or crystalline forms of salts and solvate of vortioxetine in the present invention are characterized by characteristic peaks at 2θ angles in X-ray powder diffraction patterns or directly by X-ray powder diffraction patterns. Those skilled in the art can understand that, under effects such as instrumental conditions, sample preparation and sample purity, in particular instrumental conditions, 2θ angles of characteristic peaks in X-ray powder diffraction patterns of crystals or crystalline forms of salts and solvate of vortioxetine may fluctuate within certain error ranges. It needs to be particularly pointed out that the relative intensities of X-ray diffraction peaks may also change with the change of experimental conditions, so the peak intensity order cannot be considered as the only or decisive factor. Additionally, the experimental error of 2θ angles of characteristic peaks is usually 5% or even less, and these errors should also be considered; usually for a peak an error of ±0.2° is allowed. Additionally, experimental factors such as sample preparation (e.g. sample height) may lead to overall peak shifts, therefore usually certain shift is allowed. Therefore, those skilled in the art can understand that any crystalline forms that have the same characteristic peaks or match the overall pattern to that of the present invention are within the scope of the present invention.

Unless particularly specified, "anhydrous crystal or crystalline form" in the present invention means that the crystal or crystalline form contains not more than 1.5% (w/w) or not more than 1.0% (w/w) of water as measured by thermogravimetric analysis (TGA).

In the present invention, the "$C_1$-$C_4$ alcohols" include methanol, ethanol, n-propanol, isopropanol, 1-butanol and 2-butanol.

In the present invention, the "$C_4$-$C_5$ esters" include ethyl acetate, propyl formate, isopropyl formate, methyl propionate, methyl isopropionate, propyl acetate, isopropyl acetate, ethyl propionate and ethyl isopropionate.

In the present invention, the "$C_3$-$C_4$ ketones" include acetone and butanone.

In the present invention, the "room temperature" is 10-30° C.

In the present invention, the "sonication" facilitates dissolution of samples. The detailed operation is: place the container of the suspension in an ultrasonic cleaner and sonicate at 20 Khz~40 Khz for 1-30 min (usually 5 min).

Furthermore, the present invention provides a pharmaceutical composition, which comprises a therapeutically and/or preventively effective amount of the salts or solvate of vortioxetine or crystalline forms thereof of the present invention, or the salts or solvate of vortioxetine or crystalline forms thereof of the present invention obtained by the preparation methods of the present invention and at least one pharmaceutically acceptable excipient, wherein the salts or solvate of vortioxetine or crystals or crystalline forms thereof include vortioxetine hemihydrobromide or the crystalline form thereof, the vortioxetine hydrobromide isopropanol solvate or the crystalline form thereof, vortioxetine besylate or crystalline form B thereof, vortioxetine citrate or crystalline form C thereof, vortioxetine succinate or crystalline form S thereof, vortioxetine p-toluenesulfonate or crystalline form T thereof, vortioxetine p-chlorobenzenesulfonate or crystalline form Ch thereof, vortioxetine ethanedisulfonate or crystalline form E thereof, vortioxetine α-ketoglutarate or crystalline form G thereof, vortioxetinel 1,5-naphthalenedisulfonate or crystalline form N thereof, vortioxetine 2-naphthalenesulfonate or crystalline form Na thereof, vortioxetine 3-hydroxy-2-naphthoate or crystalline form H thereof, vortioxetine 1-hydroxy-2-naphthoate or crystalline form Hy thereof, and vortioxetine oxalate or crystalline form O thereof. Optionally, the pharmaceutical composition may comprise pharmaceutically acceptable crystals, crystalline forms or amorphous forms of vortioxetine or other salts and solvate of vortioxetine, which including but not limit to the known α Form, β Form, γ Form, hydrate or ethyl acetate solvate of vortioxetine hydrobromide. Optionally, the pharmaceutical composition may comprise one or more other active pharmaceutical ingredients, which including but not limited to other antidepressants, sedatives, hypnotics, anticonvulsants, mood stabilizers, antipsychotics, drugs for treating Alzheimer's disease, immunomodulators, etc.

The pharmaceutical composition may be made into certain dosage forms. Administration routes are preferably oral administration, parenteral administration (including subcutaneous administration, intramuscular administration and intravenous administration) and rectal administration. For examples, suitable dosage forms for oral administration include tablets, capsules, granules, pulvis, pills, powders, lozenges, syrups and suspensions; suitable dosage forms for parenteral administration include aqueous or non-aqueous solutions or emulsions for injection; suitable dosage forms for rectal administration include suppositories using hydrophilic or hydrophobic carriers. Depending on the demand, the pharmaceutical composition may be made into suitable dosage forms for rapid release, delayed release or controlled release of the active ingredients.

Regarding pharmaceutically acceptable excipients in the pharmaceutical composition, for example, solid excipients include but are not limited to: diluents, e.g. starch, modified starch, lactose, powdered cellulose, microcrystalline cellulose, anhydrous calcium hydrogen phosphate, tricalcium phosphate, mannitol, sorbitol, and sugar, etc.; adhesives, e.g. Arabia gum, guar gum, gelatin, polyvinylpyrrolidone, hydroxypropyl cellulose, hydroxypropyl methylcellulose, polyethylene glycol, copolyvidone, etc.; disintegrants, e.g. starch, sodium carboxymethyl starch, sodium starch glycolate, pregelatinized starch, cross-linked polyvinyl polypyrrolidone, cross-linked sodium carboxymethylcellulose, and colloidal silica dioxide, etc.; lubricants, e.g. stearic acid, magnesium stearate, zinc stearate, sodium benzoate, and sodium acetate, etc.; glidants, e.g. colloidal silica dioxide; complex forming agents, e.g. cyclodextrin and resins of various grades; release rate controllers, e.g. hydroxypropyl cellulose, carboxymethyl cellulose, hydroxypropyl methyl cellulose, ethyl cellulose, methyl cellulose, methyl methacrylate, and wax, etc. The pharmaceutically acceptable excipients also include liquid excipients, specifically including but not limited to: aqueous solvents, alcohols or oils such as sterile water, saline, glucose solution, mannitol solution, vegetable oil, fish liver oil, ethanol, propanol, glycerin, etc. Additionally, other excipients such as polyethylene glycol and polypropylene glycol may be used. Other optional pharmaceutically acceptable excipients include but are not limited to film forming agents, plasticizers, coloring agents, flavoring agents, viscosity regulators, preservatives, antioxidants, penetrants, buffers, etc. Each excipient must be acceptable, compatible with other ingredients in the formula and non-hazardous to patients.

The pharmaceutical composition may be prepared by a method commonly known to those skilled in the art. In preparation of the pharmaceutical composition, the salts or solvate of vortioxetine or crystalline forms thereof disclosed by the present invention as the active pharmaceutical ingredient are mixed with one or more pharmaceutically acceptable excipients, and optionally with one or more other active ingredients. For example, solid dosage forms may be prepared by direct blending, granulation and other processes; liquid dosage forms may be prepared by blending, dissolution and other processes.

Particularly mentioned are tablets or capsules. Tablets or capsules may be prepared by mixing the active pharmaceutical ingredient with one or more aforesaid pharmaceutically acceptable excipients and then tabletting the resulting mixture in a routine pelleter to prepare tablets or filling the resulting mixture in capsule shells to prepare capsules. Examples of the excipients include anhydrous calcium hydrogen phosphate, PVP, PVP-VA copolymer, microcrystalline cellulose, sodium starch glycolate, corn starch, mannitol, potato starch, talc, magnesium stearate, gelatin, lactose, gum, etc. Excipients commonly used for achieving the above purposes may also be used, e.g. coloring agents, flavoring agents, and preservatives, etc.

Particularly mentioned is the wet granulation process of solid preparations. Take wet granulation for preparing tablets as an example. The preparation process is: blend dry solids (active pharmaceutical ingredient, fillers, adhesives, etc.), wet the mixture with a wetting agent [e.g. water or alcohols (e.g. ethanol)], make the wetted solid into aggregates or granules, continue the wet granulation until the required uniform particle size distribution is obtained, and then dry the obtained granules. Typically, in a high-speed shearing machine, mix the vortioxetine salts or crystals or crystalline forms thereof of the present invention, lactose, corn starch and copolyvidone with water; after granules are formed, pass these granules through sieves with appropriate meshes, dry, mix the obtained dry granules with microcrystalline cellulose, croscarmellose sodium and magnesium stearate and then perform tabletting. Optionally, the wet granulation of compounds in the present invention may be achieved by granulating with mannitol, corn starch and copolyvidone; mix the obtained granules with microcrystalline cellulose, sodium starch glycolate and magnesium stearate, and then perform tabletting. Optionally, the wet granulation of compounds in the present invention may be achieving by granulating with anhydrous calcium hydrogen phosphate, corn starch and copolyvidone; mix the obtained granules with microcrystalline cellulose, sodium starch glycolate and magnesium stearate, and then perform tabletting. Copolyvidone is a PVP-VA copolymer. Alternatively, mix the active ingredient, mannitol and microcrystalline cellulose in a fluidized bed granulating and drying machine, spray aqueous solution of hydroxypropyl cellulose to the mixture to obtain granular fine powder, mix the obtained granules with microcrystalline cellulose, sodium starch glycolate and magnesium stearate, and then perform tabletting. Alternatively, coat the tablets with an appropriate coating material, e.g. spray a solution containing the coating material onto the tablets.

Particularly mentioned are oral suspensions. One advantage of the dosage form is that patients need not to swallow solids, so it is particularly suitable for aged people who have difficulty in swallowing solids, children or patients with oral or throat injuries. Suspension is a two-phase system formed from dispersing solid granules of the active pharmaceutical ingredient in a liquid; for example, the salts or solvate of vortioxetine or crystals or crystalline forms of the present invention which maintain their original solid forms in water, aqueous carriers or alcohol-containing carriers in an oral suspension. What is well known to those skilled in the art is that other ingredients in the oral suspension may include buffers, surfactants, viscosity regulators, preservatives, antioxidants, coloring agents, flavoring agents, and taste masks, etc.

Particularly mentioned is that the vortioxetine hemihydrobromide and the crystalline form thereof of the present invention, for their excellent thermal stability, particularly stability in water and ethanol, they are more suitable for solid formulations using wet granulation process or for oral suspensions, providing better phase stability in pharmaceutical manufacturing and/or storage.

Furthermore, the present invention provides uses of the salts or solvate of vortioxetine or crystals and crystalline forms thereof in the manufacture of drugs for treating and/or preventing diseases selected from affective disorders, major depression, routine anxiety disorder, obsessive compulsive disorder, panic disorder, post-traumatic stress disorder, depressions associated with cognitive deficits, Alzheimer's disease and anxiety disorder, depression with residual symptoms, chronic pain, eating disorders, alcoholism, nicotine or carbohydrate addiction, drug abuse, alcohol or drug abuse.

Furthermore, the present invention provides a method for treating and/or preventing diseases selected from affective disorders, major depression, routine anxiety disorder, obsessive compulsive disorder, panic disorder, post-traumatic stress disorder, depressions associated with cognitive deficits, Alzheimer's disease and anxiety disorder, depression with residual symptoms, chronic pain, eating disorders, alcoholism, nicotine or carbohydrate addiction, drug abuse, alcohol or drug abuse, which comprises administering to a patient in need a therapeutically and/or preventatively effective amount of the salts or solvate of vortioxetine or crystals and crystalline forms of the present invention or the pharmaceutical composition of the present invention, wherein the patients are mammals including human beings. Conveniently, the salts or solvate of vortioxetine or crystals and crystalline forms of the present invention are administered in unit dose comprising about 1-50 mg of vortioxetine hemihydrobromide or the crystals or the crystalline forms thereof, the vortioxetine hydrobromide isopropanol solvate or the crystal thereof, vortioxetine besylate or crystalline form B thereof, vortioxetine citrate or crystalline form C thereof, vortioxetine succinate or crystalline form S thereof, vortioxetine p-toluenesulfonate or crystalline form T thereof, vortioxetine p-chlorobenzenesulfonate or crystalline form Ch thereof, vortioxetine ethanedisulfonate or crystalline form E thereof, vortioxetine α-ketoglutarate or crystalline form G thereof, vortioxetinel 1,5-naphthalenedisulfonate or crystalline form N thereof, vortioxetine 2-naphthalenesulfonate or crystalline form Na thereof, vortioxetine 3-hydroxy-2-naphthoate or crystalline form H thereof, vortioxetine 1-hydroxy-2-naphthoate or crystalline form Hy thereof, and vortioxetine oxalate or crystalline form O thereof (calculated as free base). The daily dosage is usually 1-20 mg, e.g. approximately 1-10 mg, approximately 5-10 mg, approximately 10-20 mg or approximately 10-15 mg; particularly mentioned is that the daily dosage is 2.5 mg, 5 mg. 10 mg, 15 mg or 20 mg.

EXAMPLES

Figure 1:
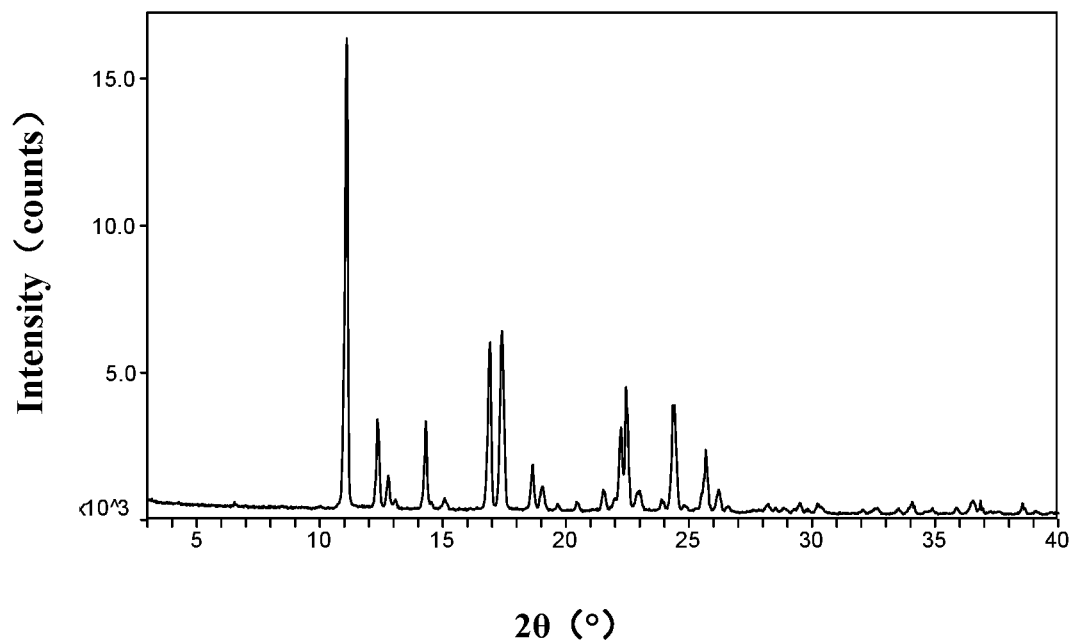
FIG. 1 is the XRPD pattern of vortioxetine prepared according to example 24 in patent document WO2007/144005A1.

The following examples are given for further understanding the present invention but are not used for limiting the disclosure of the present invention. The examples describe in detail preparation methods and uses of salts, solvates and crystalline forms thereof of vortioxetine in the present invention. It will be apparent to those skilled in the art from this disclosure that various modifications can be made to materials and methods without departing from the scope of the present invention.

Instruments and methods used for data collection:

X-ray powder diffraction (XRPD) was performed on a Bruker D8 Advance Diffractometer configured with a θ-2θ goniometer, a Mo monochromator and a Lynxeye detector. The collection software is Diffrac Plus XRPD Commander. Before using, the instrument was performance checked using the provided standard (usually corundum). The following testing conditions were used: 2θ scan range, 3-40'; step size, 0.02°; speed, 0.2 s/step. Testing procedure: using a Cu-Kα X-ray with a wavelength of 1.54 nm, the sample was analyzed on a SiP non-reflective plate at room temperature at 40 kV and 40 mA. Unless particularly specified, samples had not been grinded prior to analysis.

Differential scanning calorimetry (DSC) data were collected using TA Instruments Q200 MDSC. The instrument control software was Thermal Advantage, and the analytical software was Universal Analysis. Usually, 1-10 mg of the sample was placed in an uncovered (unless particularly specified) aluminum pan and heated at a rate of 10° C./min from 0° C. to 250° C. under the protection of dry $N_2$ at a flow rate of 40 mL/min while the TA software was recording heat changes of the sample during the heating process. In the present application, melting points are reported as the starting temperature.

Thermogravimetric analysis (TGA) data were collected using TA Instruments Q500 MDSC. The instrument control software was Thermal Advantage, and the analytical software was Universal Analysis. Usually, 5-15 mg of the sample was placed in a platinum pan and, by segmental high-resolution detection, the sample was heated at a rate of 10° C./min from room temperature to 350° C. under the protection of dry $N_2$ at a flow rate of 40 mL/min while the TA software was recording weight changes of the sample during the heating process.

Dynamic vapor sorption (DVS) data were collected using TA Instruments Q5000 TGA. The instrument control software was Thermal Advantage, and the analytical software was Universal Analysis. Usually, 1-10 mg of the sample was placed in a platinum pan and the weight change of the sample during experiments was recorded. The relative humidity was usually programmed to change from 20% to 80% and then back to 20%, and an isothermal sorption curve could be generated. Depending on specific situations, different sorption and desorption procedures might be used.

Infrared spectrometry (IR) data were collected using BrukerTensor 27. OPUS was used both for instrument control and data analysis. Usually, the infrared absorption spectra were collected over 600-4000 $cm^{-1}$ using ATR equipment. Both samples and the blank background were scanned for 16 s. The instrument resolution was 4 $cm^{-1}$.

$^1$H Nuclear magnetic resonance spectrum ($^1$HNMR) data were collected using Bruker Avance II DMX 400M HZ nuclear magnetic resonance spectrometer. 1-5 mg of sample was dissolved in 0.5 mL of deuterium-substituted dimethyl sulfoxide to produce a 2-10 mg/mL solution.

Element analysis (C, H, N, O, S) data were collected by CE-400 with horizontal injection burning equipped with a thermal conductivity detector. Sample volume: 1-5 mg; analytical time: for analysis of C, H and N, less than 5 min; range: 100 ppm to 100%.

High performance liquid chromatography (HPLC) data were collected using Waters 2487/2695 under the following conditions: C8 column (250 mm×4.6 mm); column temperature, 35° C.; wavelength, 230 nm; flow rate, 1.5 mL/min; injection volume, 10 μL; running time, 40 min. The buffer was prepared by dissolving 8.7 g of sodium lauryl sulfate and 3.3 mL of phosphoric acid solution in 1 L of water and then adjusting the pH value with NaOH to 2.5. Mobile phase A was acetonitrile-buffer (48:52); mobile phase B was acetonitrile-buffer (70:30). The gradient is shown in Table 1:

TABLE 1

| HPLC gradient table | | |
|---|---|---|
| Time (min) | Mobile phase A (%) | Mobile phase B (%) |
| 0 | 95 | 5 |
| 5 | 80 | 20 |
| 33 | 30 | 70 |
| 35 | 30 | 70 |
| 36 | 95 | 5 |
| 40 | 95 | 5 |

Unless particularly specified, all examples were conducted at room temperature.

Unless particularly specified, all reagents used in the examples were commercially purchased.

Unless particularly specified, ratios of components in the mixed solvents in the examples were volume ratios.

Sonication in the examples was conducted at 40 Khz for 5 min.

Preparation Example 1

Vortioxetine was synthesized by reference to the preparation process in example 24 in patent document WO2007/144005A1. The process is specified as follows: Under nitrogen protection, 200 mL of toluene, 40.76 g of sodium tert-butoxide, 0.33 g of Pd(dba)2[Bis(dibenzylideneacetone) palladium] and 0.68 g of rac-BINAP(2,2'-bis(diphenylphosphino)-1,1'-binaphthyl) were successively added to a 500 mL four-neck flask, and then stirring was started, followed by addition of 19.54 g of 2,4-dimethylbenzenethiol. white precipitation came out. 42.00 g of 2-bromo-lodobenzene was added, kept the reflux reaction heated for 5 h; the reaction mixture was cooled to room temperature and filtered; removed insoluble matters, the filtrate was poured back into a 500 mL four-neck flask, followed by addition of 42.20 g of anhydrous piperazine, 40.76 g of sodium tert-butoxide, 0.33 g of Pd(dba)$_2$ and 0.68 g of rac-BINAP; after refluxing for 2 h, the reaction completed.

The reaction mixture was cooled to room temperature, and 100 mL of water was added for extraction. The organic phase was filtered, and the filtrate was washed with 3×80 mL of saturated salt solution. Heated the organic phase to 70° C., added 16.50 mL of 48% hydrobromic acid (145.9 mmol) and 8.3 mL of water, stirred for 30 min, then cooled to room temperature, kept it at room temperature for 2 h, filtered and washed with toluene. After suction filtration, the filter cake was dried under vacuum at 50° C. for 10 h. 40.18 g of off-white 1-[2-(2,4-dimethylphenylsulfanyl) phenyl] piperazine hydrobromide, i.e. vortioxetine hydrobromide solid was obtained. The molar yield was 75%.

$^1$H-NMR (300 MHz,
DMSO-d6)2.10-2.30 (m, 1H), 2.34 (s, 3H), 2.38 (s, 3H), 3.11 (m, 8H), 6.52-6.54 (m, 1H), 6.87-6.90 (m, 1H), 7.04-7.10 (m, 3H), 7.17 (s, 1H), 7.28 (m, 1H).

40.18 g of vortioxetine hydrobromide obtained in the above step was dissolved in 200 mL of water, followed by addition of 200 mL of dichloromethane and the pH of the solution was adjusted with 15% sodium hydroxide solution to 9-10. The mixture was kept isothermal for 30 min, and it separated into two layers. The aqueous phase was extracted once with 100 mL of dichloromethane, and then combined with the organic phases. The combined mixture was washed with 100 mL of water. The organic phase was separated and, 5 g of anhydrous sodium sulfate was added for drying, then filtered. The filtered solution was concentrated until the solvent was removed. 29.7 g off-white crystals of 1-[2-(2, 4-dimethylphenylsulfanyl) phenyl] piperazine, i.e. vortioxetine, were obtained. The molar yield was 94.0%.

The X-ray powder diffraction pattern of the obtained vortioxetine sample is shown in FIG. 1, which is basically the same as that of the compound provided by WO2007/144005A1. $^1$H-NMR data indicates the product is vortioxetine.

$^1$H-NMR (300 MHz, DMSO-d6) 2.10-2.30 (m, 1H), 2.34 (s, 3H), 2.38 (s, 3H), 3.11 (m, 8H), 6.52-6.54 (m, 1H),
6.87-6.90 (m, 1H), 7.04-7.10 (m, 3H), 7.17 (s, 1H), 7.28 (m, 1H).

Preparation Example 2

To 5.00 g (16.8 mmol) of vortioxetine, 125 mL of ethyl acetate was added, heated the solution to 70° C. and the solids were completely dissolved. With the temperature maintained at 70° C. and stirring, 3.4 g of hydrobromic acid (40% w/w, 16.8 mmol) was slowly added dropwise to the vortioxetine solution; solids precipitated out during the dropwise-addition process and the solution gradually turned viscous; 25 mL of ethyl acetate was added, and the solution became flowable; after moved to room temperature and stirred for 4 h, the mixture was filtered under reduced pressure. After drying under vacuum at 40° C. for 24 h, the β Form of vortioxetine hydrobromide was obtained. The yield was 2.00 g (5.3 mmol); the percent yield was 31.5%.

Figure 7:
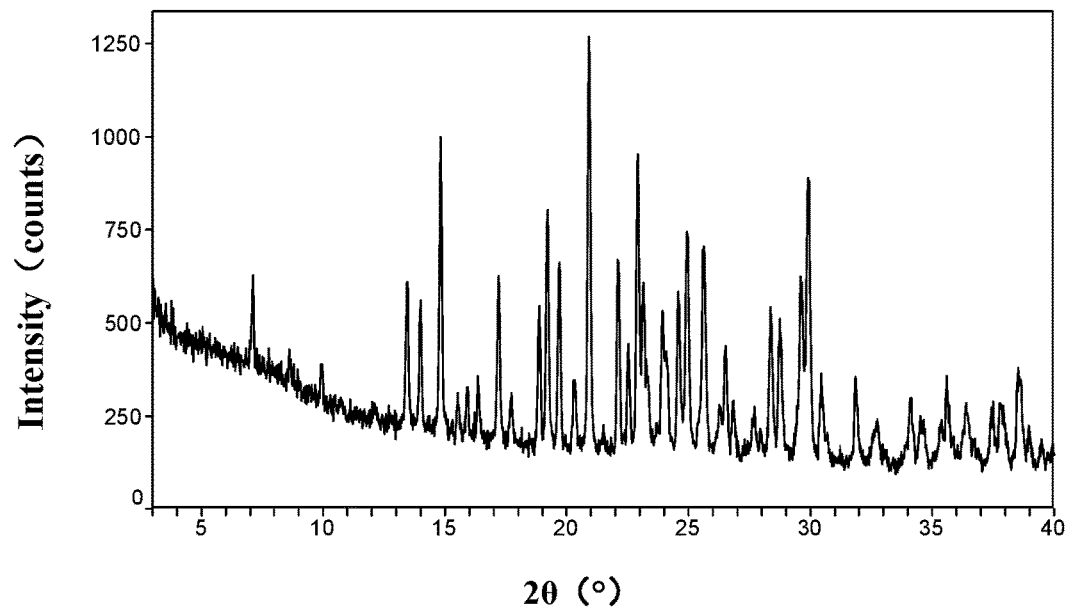
FIG. 7 is the XRPD pattern of the β Form of vortioxetine hydrobromide prepared in example 2.

The XRPD pattern is shown in FIG. 7, which is consistent with the XRPD pattern of the β Form of vortioxetine hydrobromide provided in WO2007/144005A1.

Example 1

8.00 g (26.8 mmol) of vortioxetine was dissolved in 122 mL of ethanol by sonication in a 250 mL round-bottom flask; 2.70 g of hydrobromic acid (40% w/w, 13.3 mmol) was dissolved in 16 mL of ethanol by sonication; with stirring, the hydrobromic acid solution was slowly added dropwise to the vortioxetine solution; solids precipitated out during the dropwise-addition process; the solvent was removed by rotary evaporation at 40° C.; after drying under vacuum at 40° C. for 24 h, 8.91 g (13.1 mmol) of white solids of the vortioxetine hemihydrobromide were obtained. The percent yield was 98.5%.

HPLC characterization indicates the white solids are the vortioxetine hemihydrobromide, formed from vortioxetine and hydrogen bromide at a molar ratio of 2:1. The detailed characterization procedure is: Using vortioxetine as the reference substance, the obtained white solids were accurately weighed and assayed by HPLC to get the weight percent of vortioxetine in the white solids. The weight percent of hydrogen bromide was obtained by subtracting the weight percent of vortioxetine from one. According to the calculation result, the molar ratio of vortioxetine to hydrogen bromide is 2:1 in the white solids.

In addition, the white solids were analyzed by elemental analysis. Elemental compositions in the white solids are: 63.53% C, 6.59% N, and 8.42% H (theoretical values for vortioxetine and hydrogen bromide salt formation at a molar ratio of 2:1 are 63.68% C, 6.63% N, and 8.25% H), verifying that the white solids are the vortioxetine hemihydrobromide formed from vortioxetine and hydrogen bromide at a molar ratio of 2:1.

Example 2

14.24 g (47.7 mmol) of vortioxetine was dissolved in 148 mL of isopropyl acetate by sonication; 2.40 g of hydrobromic acid (40% w/w, 11.9 mmol) was dissolved in 16 mL of isopropyl acetate by sonication; with stirring, the hydrobromic acid solution was slowly added dropwise to the vortioxetine solution; solids precipitated out during the dropwise-addition process; the solvent was removed by rotary evaporation at 10° C.; 60 ml of isopropyl acetate was added, the resulting mixture was stirred for 10 min and filtered; after drying under vacuum at room temperature for 24 h, 7.95 g (11.7 mmol) of white solids of the vortioxetine hemihydrobromide were obtained. The percent yield was 98.9%.

HPLC characterization indicates that the vortioxetine hemihydrobromide is formed from vortioxetine and hydrogen bromide at a molar ratio of 2:1.

Elemental analysis: 63.74% C, 6.44% N, 8.32% H, (theoretical values for vortioxetine and hydrogen bromide salt formation at a molar ratio of 2:1: 63.68% C, 6.63% N, 8.25% H).

Example 3

47.80 g (160.2 mmol) of vortioxetine was dissolved in 122 mL of acetone by sonication; 3.23 g of hydrobromic acid (40% w/w, 16.0 mmol) was dissolved in 16 mL of acetone by sonication; with stirring, the hydrobromic acid solution was slowly added dropwise to the vortioxetine solution; solids precipitated out during the dropwise-addition process; the solvent was removed by rotary evaporation at 50° C.; 70 ml of acetone was added, the resulting mixture was stirred for 10 min and filtered; after drying under vacuum at 40° C. for 24 h, 10.59 g (15.6 mmol) of white solids of the vortioxetine hemihydrobromide were obtained. The percent yield was 97.8%.

HPLC characterization indicates that the vortioxetine hemihydrobromide is formed from vortioxetine and hydrogen bromide at a molar ratio of 2:1.

Elemental analysis: 63.28% C, 6.44% N, 8.38% H, (theoretical values for vortioxetine and hydrogen bromide salt formation at a molar ratio of 2:1: 63.68% C, 6.63% N, 8.25% H).

Example 4

5.00 g (16.8 mmol) of vortioxetine was dissolved in 75 mL of ethanol by sonication (the concentration of the vortioxetine solution in ethanol was 1 times of its solubility in ethanol at the crystallization temperature (room temperature)); 1.70 g of hydrobromic acid (40% w/w, 8.4 mmol) was dissolved in 10 mL of ethanol by sonication (the concentration of the hydrobromic acid solution in ethanol was 1 times of its solubility in ethanol at the crystallization temperature (room temperature)); with stirring, the hydrobromic acid solution was slowly added dropwise to the vortioxetine solution; solids precipitated out during the dropwise-addition process; after stirred at room temperature for 2 h, the mixture was filtered under reduced pressure; after drying under vacuum at 40° C. for 24 h, the vortioxetine hemihydrobromide crystalline form of the present invention was obtained. The yield was 5.31 g (7.8 mmol); the percent yield was 93.2%.

Figure 2:
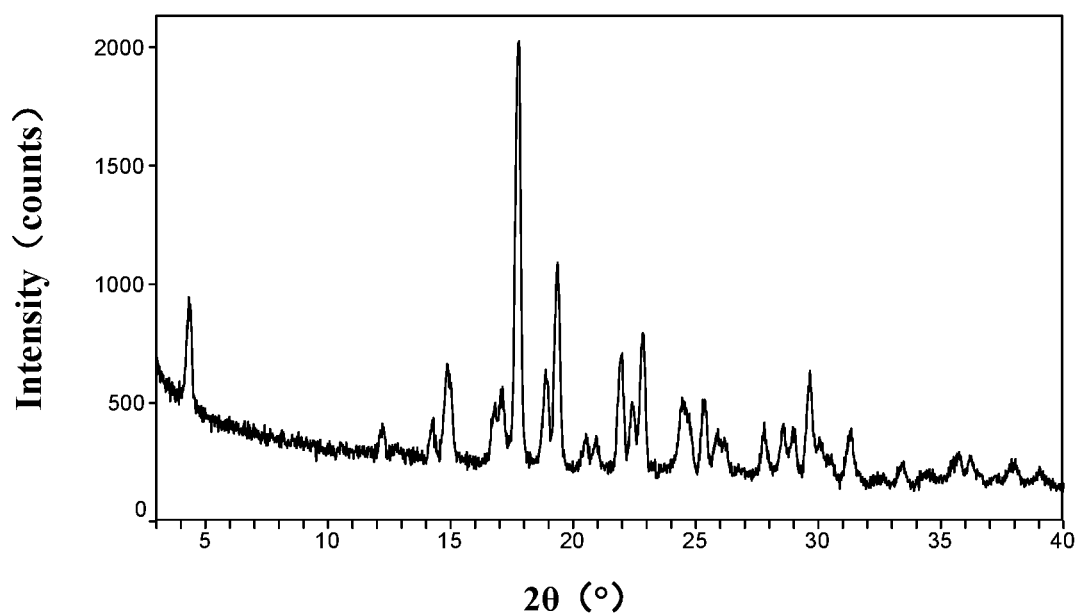
FIG. 2 is the XRPD pattern of the vortioxetine hemihydrobromide crystalline form of the present invention.

The XRPD pattern is shown in FIG. 2.

Figure 3:
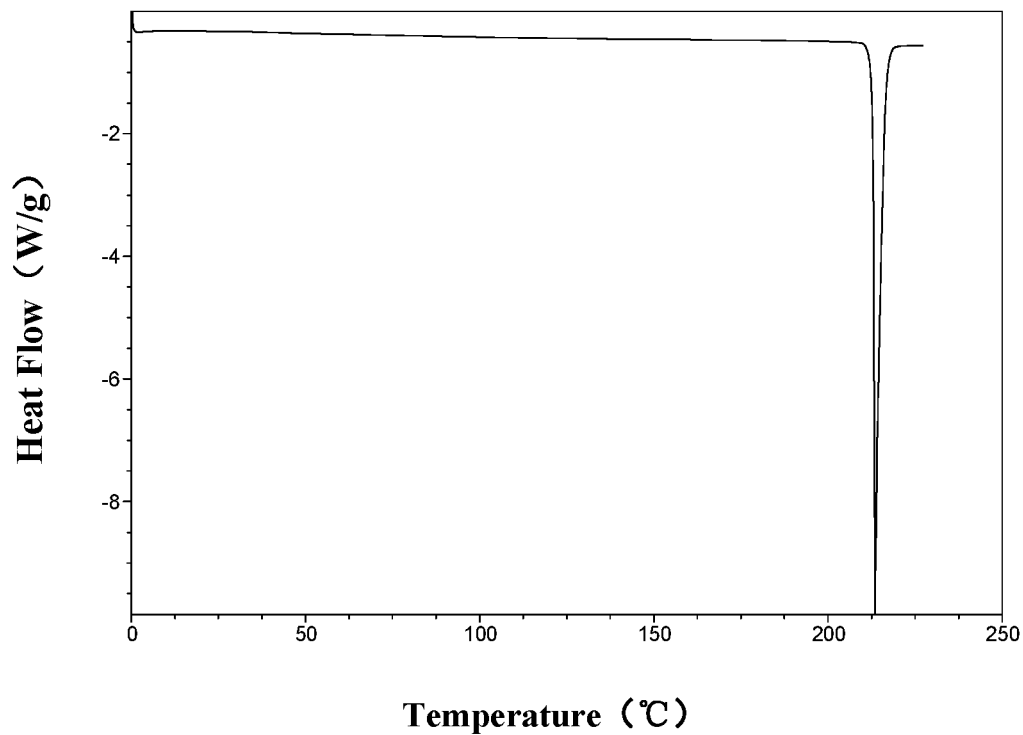
FIG. 3 is the DSC thermogram of the vortioxetine hemihydrobromide crystalline form of the present invention.

The DSC thermogram is shown in FIG. 3, indicating melting decomposition began at 213° C.

Figure 4:
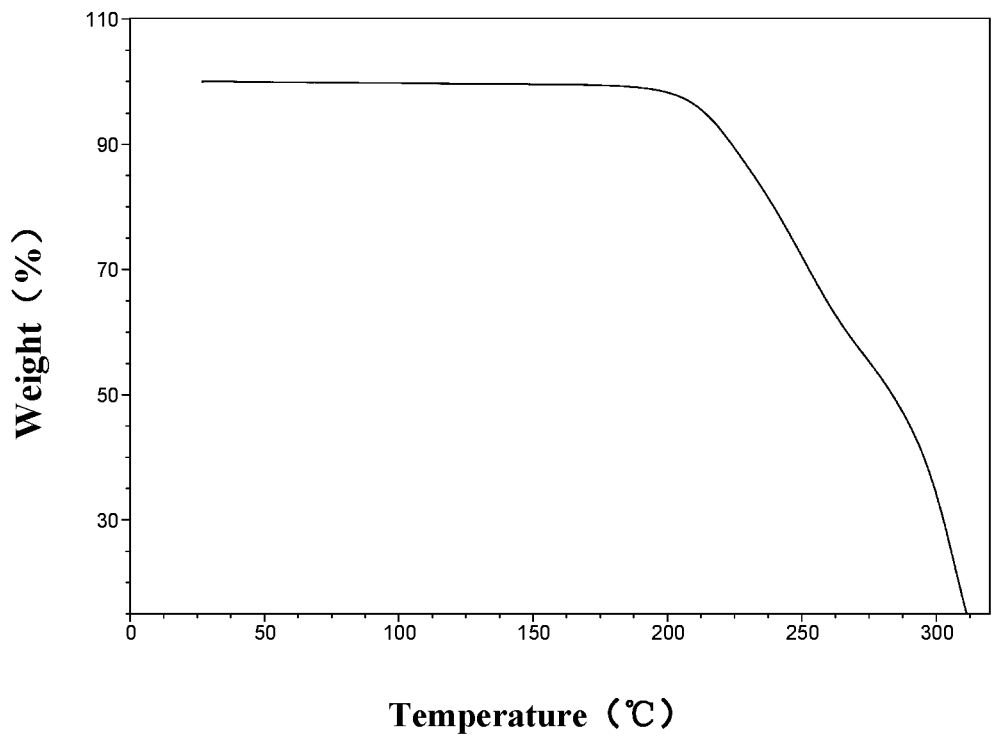
FIG. 4 is the TGA thermogram of the vortioxetine hemihydrobromide crystalline form of the present invention.

The TGA thermogram is shown in FIG. 4, indicating basically no weight loss occurred before 150° C.; the solids were anhydrous and the decomposition temperature was about 216° C.

Figure 5:
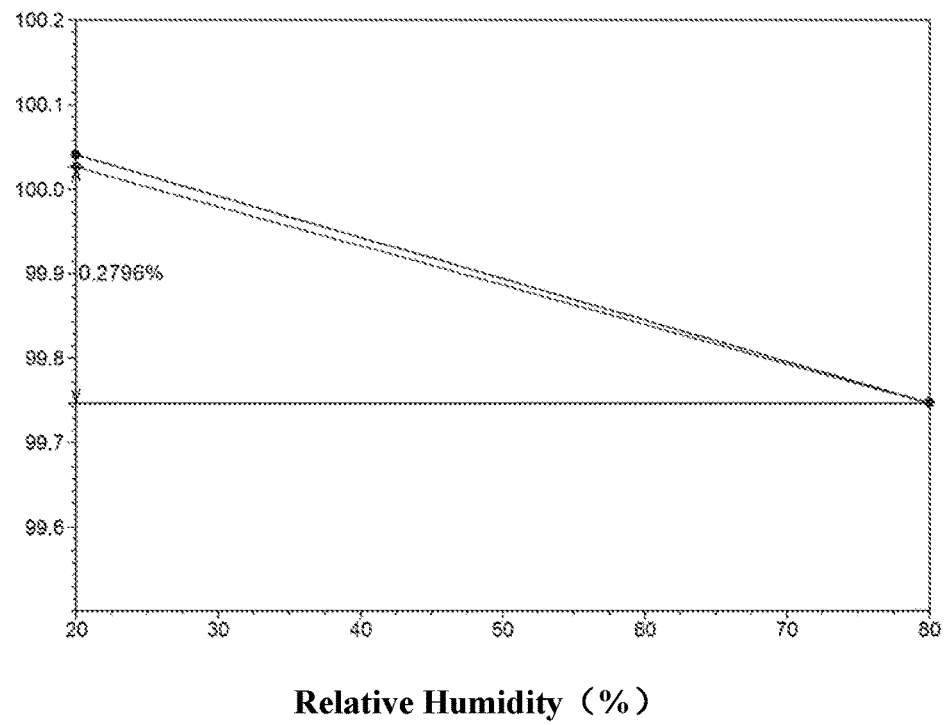
FIG. 5 is the isothermal sorption curve of the vortioxetine hemihydrobromide crystalline form of the present invention.

The isothermal sorption curve is shown in FIG. 5, indicating the weight change within the relative humidity range of 20%-80% was 0.28%.

Figure 6:
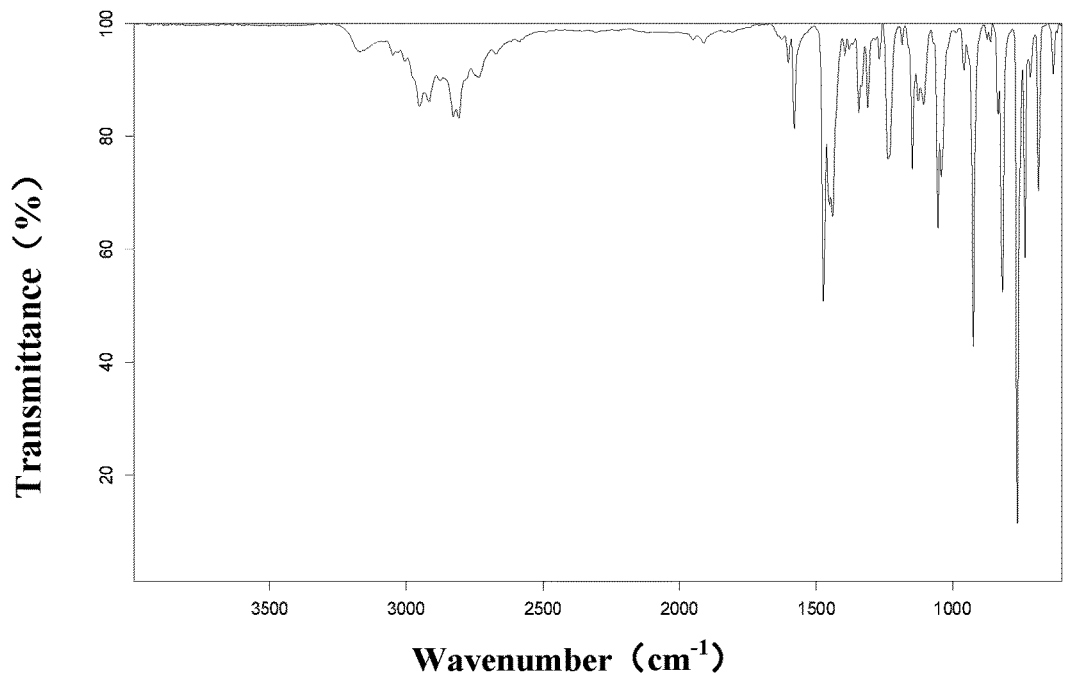
FIG. 6 is the IR spectrum of the vortioxetine hemihydrobromide crystalline form of the present invention.

The IR spectrum is shown in FIG. 6.

HPLC characterization indicates that the vortioxetine hemihydrobromide is formed from vortioxetine and hydrogen bromide at a molar ratio of 2:1.

Example 5

10.04 g (33.6 mmol) of vortioxetine was dissolved in 150 mL of ethanol by sonication (the concentration of the vortioxetine solution in ethanol was 1 times of its solubility in ethanol at the crystallization temperature (50° C.)); 1.70 g of hydrobromic acid (40% w/w, 8.4 mmol) was dissolved in 20 mL of ethanol by sonication (the concentration of the hydrobromic acid solution in ethanol was 0.5 times of its solubility in ethanol at the crystallization temperature (50° C.)); with stirring, the hydrobromic acid solution was slowly added dropwise to the vortioxetine solution; solids precipitated out during the dropwise-addition process; after stirred at 50° C. for 15 h, the mixture was filtered under reduced pressure; after drying under vacuum at 40° C. for 24 h, the vortioxetine hemihydrobromide crystalline form of the present invention was obtained. The yield was 4.97 g (7.3 mmol); the percent yield was 87.2%.

Example 6

27.2 g (91.1 mmol) of vortioxetine was dissolved in 408 mL of ethanol by sonication (the concentration of the vortioxetine solution in ethanol was 1 times of its solubility in ethanol at the crystallization temperature (room temperature)); 1.85 g of hydrobromic acid (40% w/w, 9.1 mmol) was dissolved in 11 mL of ethanol by sonication (the concentration of the hydrobromic acid solution in ethanol was 1 times of its solubility in ethanol at the crystallization temperature (room temperature)); with stirring, the hydrobromic acid solution was slowly added dropwise to the vortioxetine solution; solids precipitated out during the dropwise-addition process; after stirred at room temperature for 4 h, the mixture was filtered under reduced pressure; after drying under vacuum at 40° C. for 24 h, the vortioxetine hemihydrobromide crystalline form of the present invention was obtained. The yield was 5.29 g (7.8 mmol); the percent yield was 85.3%.

Example 7

5.02 g (16.8 mmol) of vortioxetine was dissolved in 75 mL of ethanol by sonication (the concentration of the vortioxetine solution in ethanol was 0.1 times of its solubility in ethanol at the crystallization temperature (−10° C.)); 1.68 g of hydrobromic acid (40% w/w, 8.3 mmol) was dissolved in 13 mL of ethanol by sonication (the concentration of the hydrobromic acid solution in ethanol was 0.8 times of its solubility in ethanol at the crystallization temperature (−10° C.)); with stirring, the hydrobromic acid solution was slowly added dropwise to the vortioxetine solution; solids precipitated out during the dropwise-addition process; after stirred at −10° C. for 48 h, the mixture was filtered under reduced pressure; after drying under vacuum at 40° C. for 24 h, the vortioxetine hemihydrobromide crystalline form of the present invention was obtained. The yield was 3.78 g (5.6 mmol); the percent yield was 67.1%.

Example 8

7.44 g (24.9 mmol) of vortioxetine was dissolved in 91 mL of methanol by sonication (the concentration of the vortioxetine solution in methanol was 0.8 times of its solubility in methanol at the crystallization temperature (room temperature)); 1.68 g of hydrobromic acid (40% w/w, 8.3 mmol) was dissolved in 20 mL of methanol by sonication (the concentration of the hydrobromic acid solution in methanol was 0.6 times of its solubility in methanol at the crystallization temperature (room temperature)); with stirring, the vortioxetine solution was slowly added dropwise to the hydrobromic acid solution; solids precipitated out during the dropwise-addition process; after stirred at room temperature for 3 h, the mixture was filtered under reduced pressure; after drying under vacuum at 40° C. for 24 h, the vortioxetine hemihydrobromide crystalline form of the present invention was obtained. The yield was 4.95 g (7.3 mmol); the percent yield was 87.9%.

Example 9

7.25 g (24.3 mmol) of vortioxetine was dissolved in 220 mL of ethanol by sonication (the concentration of the vortioxetine solution in ethanol was 0.5 times of its solubility in ethanol at the crystallization temperature (room temperature)); 2.45 g of hydrobromic acid (40% w/w, 12.1 mmol) was dissolved in 18 mL of ethanol by sonication (the concentration of the hydrobromic acid solution in ethanol was 0.8 times of its solubility in ethanol at the crystallization temperature (room temperature)); with stirring, the hydrobromic acid solution was slowly added dropwise to the vortioxetine solution; solids precipitated out during the dropwise-addition process; after stirred at room temperature for 1 h, the mixture was filtered under reduced pressure; after drying under vacuum at 40° C. for 24 h, the vortioxetine hemihydrobromide crystalline form of the present invention was obtained. The yield was 7.28 g (10.7 mmol); the percent yield was 88.7%.

Example 10

5.03 g (16.9 mmol) of vortioxetine was dissolved in 76 mL of isopropanol by sonication; 1.70 g of hydrobromic acid (40% w/w, 8.4 mmol) was dissolved in 10 mL of isopropanol by sonication; with stirring, the hydrobromic acid solution was slowly added dropwise to the vortioxetine solution; solids precipitated out during the dropwise-addition process; after stirred at room temperature for 2 h, the mixture was filtered under reduced pressure; after drying under vacuum at 40° C. for 24 h, the vortioxetine hemihydrobromide crystalline form of the present invention was obtained. The yield was 4.95 g (7.3 mmol); the percent yield was 86.9%.

Example 11

5.11 g (17.1 mmol) of vortioxetine was dissolved in 751 mL of ethyl acetate by sonication (the concentration of the vortioxetine solution in ethyl acetate was 0.2 times of its solubility in ethyl acetate at the crystallization temperature (50° C.)); 1.73 g of hydrobromic acid (40% w/w, 8.6 mmol) was dissolved in 10 mL of ethyl acetate by sonication (the concentration of the hydrobromic acid solution in ethyl acetate was 0.3 times of its solubility in ethyl acetate at the crystallization temperature (50° C.)); with stirring, the hydrobromic acid solution was slowly added dropwise to the vortioxetine solution; solids precipitated out during the dropwise-addition process; after stirred at 50° C. for 4 h, the mixture was filtered under reduced pressure; after drying under vacuum at 40° C. for 24 h, the vortioxetine hemihydrobromide crystalline form of the present invention was obtained. The yield was 3.20 g (4.7 mmol); the percent yield was 55.2%.

Example 12

5.05 g (16.9 mmol) of vortioxetine was dissolved in 408 mL of acetone by sonication (the concentration of the vortioxetine solution in acetone was 0.4 times of its solubility in acetone at the crystallization temperature (−10° C.)); 1.70 g of hydrobromic acid (40% w/w, 8.4 mmol) was dissolved in 10 mL of acetone by sonication (the concentration of the hydrobromic acid solution in acetone was 0.3 times of its solubility in acetone at the crystallization temperature (−10° C.)); with stirring, the hydrobromic acid solution was slowly added dropwise to the vortioxetine solution; solids precipitated out during the dropwise-addition process; after stirred at −10° C. for 25 h, the mixture was filtered under reduced pressure; after drying under vacuum at 40° C. for 24 h, the vortioxetine hemihydrobromide crystalline form of the present invention was obtained. The yield was 4.30 g (6.3 mmol); the percent yield was 75.5%.

Example 13

4.96 g (16.6 mmol) of vortioxetine was dissolved in 94 mL of ethanol by sonication (the concentration of the vortioxetine solution in ethanol was 0.8 times of its solubility in ethanol at the crystallization temperature (50° C.)); 1.67 g of hydrobromic acid (40% w/w, 8.3 mmol) was dissolved in 20 mL of ethanol by sonication (the concentration of the hydrobromic acid solution in ethanol was 0.5 times of its solubility in ethanol at the crystallization temperature (50° C.)); with stirring, the vortioxetine solution was slowly added dropwise to the hydrobromic acid solution; solids precipitated out during the dropwise-addition process; after stirred at 50° C. for 4 h, the mixture was filtered under reduced pressure; after drying under vacuum at 40° C. for 24 h, the vortioxetine hemihydrobromide crystalline form of the present invention was obtained. The yield was 4.56 g (6.7 mmol); the percent yield was 81.5%.

Example 14

5.02 g (16.8 mmol) of vortioxetine was dissolved in 75 mL of ethanol by sonication (the concentration of the vortioxetine solution in ethanol was 1 times of its solubility in ethanol at the crystallization temperature (room temperature)); 1.69 g of hydrobromic acid (40% w/w, 8.4 mmol) was dissolved in 10 mL of ethanol by sonication (the concentration of the hydrobromic acid solution in ethanol was 1 times of its solubility in ethanol at the crystallization temperature (room temperature)); with stirring, the hydrobromic acid solution was slowly added dropwise to the vortioxetine solution; solids precipitated out during the dropwise-addition process; after stirred at room temperature for 1 h, the mixture was filtered under reduced pressure; after drying under vacuum at 40° C. for 24 h, the vortioxetine hemihydrobromide crystalline form of the present invention was obtained. The yield was 5.19 g (7.7 mmol); the percent yield was 91.6%.

Example 15

5.00 g (16.8 mmol) of vortioxetine was dissolved in 75 mL of ethanol by sonication (the concentration of the vortioxetine solution in ethanol was 1 times of its solubility in ethanol at the crystallization temperature (room temperature)); 1.69 g of hydrobromic acid (40% w/w, 8.4 mmol) was dissolved in 20 mL of ethanol by sonication (the concentration of the hydrobromic acid solution in ethanol was 0.5 times of its solubility in ethanol at the crystallization temperature (room temperature)); with stirring, the hydrobromic acid solution was slowly added dropwise to the vortioxetine solution; solids precipitated out during the dropwise-addition process; after stirred at room temperature for 48 h, the mixture was filtered under reduced pressure; after drying under vacuum at 40° C. for 24 h, the vortioxetine hemihydrobromide crystalline form of the present invention was obtained. The yield was 5.00 g (7.4 mmol); the percent yield was 88.3%.

HPLC characterizations of the samples prepared in examples 5 to 15 indicate that the vortioxetine hemihydrobromide is formed from vortioxetine and hydrogen bromide at a molar ratio of 2:1. The samples in examples 5 to 15 and the sample in example 4 have the same or similar XRPD patterns, DSC thermograms, TGA thermograms and IR spectra (not shown), indicating they are the same crystalline form.

Example 16

14.24 g (47.7 mmol) of vortioxetine was dissolved in 100 mL of isopropanol by sonication; 9.6 g of hydrobromic acid (40% w/w, 47.4 mmol) was dissolved in 16 mL of isopropanol: water (5:1) mixed solution by sonication; with stirring, the hydrobromic acid solution was slowly added dropwise to the vortioxetine solution; solids precipitated out during the dropwise-addition process; the solvents were removed by rotary evaporation at 10° C., then 60 ml of isopropanol was added, the resulting mixture was stirred for 10 min and filtered; after drying under vacuum at room temperature for 24 h, 20.0 g of white solid of the vortioxetine hydrobromide isopropanol solvate was obtained. The percent yield was 96.0%.

$^1$H-NMR: (400MH, DMSO-d6) δ(ppm):
1.03 (d, 6H, J=6.0 Hz), 2.24 (s, 3H), 2.33 (s, 3H), 3.18 (m, 4H), 3.26 (m, 4H), 3.76-3.79 (m, 1H), 6.41 (d, 1H, J=7.6 Hz), 6.95-6.99 (m, 1H), 7.04-7.10 (m, 3H), 7.25-7.35 (m, 1H), 8.72 (s, 2H)

Example 17

15.00 g (50.4 mmol) of vortioxetine was dissolved in 125 mL of isopropanol by sonication; 20.24 g of hydrobromic acid (40% w/w, 100.00 mmol) was dissolved in isopropanol: water (2:1) mixed solution by sonication; with stirring, the hydrobromic acid solution was slowly added dropwise to the vortioxetine solution; solids precipitated out during the dropwise-addition process; the solvents were removed by rotary evaporation at 10° C., then 60 ml of isopropanol was added, the resulting mixture was stirred for 10 min and filtered; after drying under vacuum at room temperature for 24 h, 20.91 g of white solids of the vortioxetine hydrobromide isopropanol solvate were obtained. The percent yield was 95.2%.

Its $^1$H-NMR spectrum is consistent with that of the sample prepared in example 16.

Example 18

5.01 g (16.8 mmol) of vortioxetine was dissolved in 18 mL of isopropanol by stirring at 70° C. (the concentration of the vortioxetine solution in isopropanol was 1 times of its solubility in isopropanol at 70° C.); 3.38 g of hydrobromic acid (40% w/w, 16.7 mmol) was dissolved in 2 mL of isopropanol by stirring at 70° C. (the concentration of the hydrobromic acid solution in isopropanol was 1 times of its solubility in isopropanol at 70° C.); with stirring, the hydrobromic acid solution was slowly added dropwise to the vortioxetine solution; after completion of dropwise addition, the mixture was stirred for 10 min at 70° C. to produce a suspension; then the suspension was stirred at room temperature for 1 h and filtered; the filter cake was dried under vacuum at 20° C. for 10 h. The crystalline vortioxetine hydrobromide isopropanol solvate of the present invention was obtained. The yield was 7.03 g; the percent yield was 95.8%.

Its $^1$H-NMR spectrum is consistent with that of the sample prepared in example 16.

Figure 8:
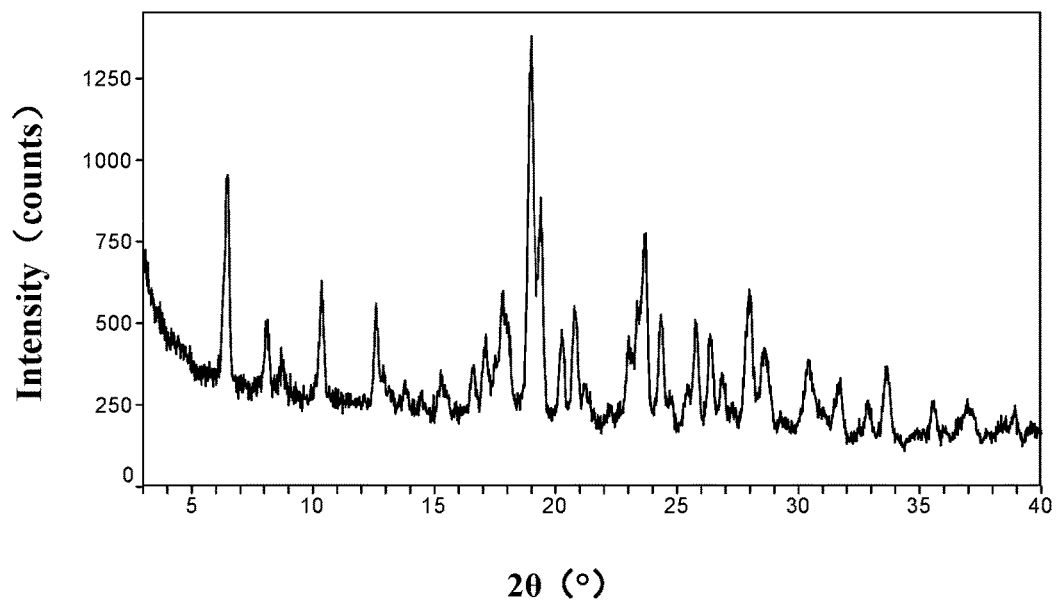
FIG. 8 is the XRPD pattern of the crystal of the vortioxetine hydrobromide isopropanol solvate of the present invention.

The XRPD pattern is shown in FIG. 8.

Figure 9:
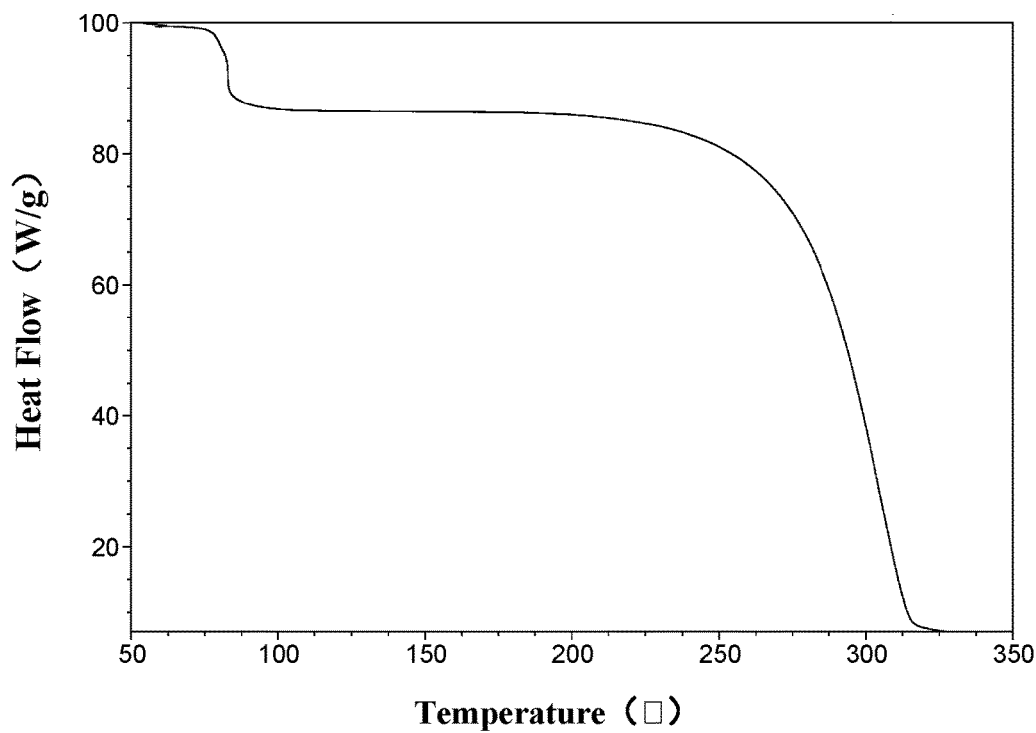
FIG. 9 is the TGA thermogram of the crystal of the vortioxetine hydrobromide isopropanol solvate.

The TGA thermogram is shown in FIG. 9, indicating: a weight loss of 13.6% occurred before 150° C., approximately every molecule of the vortioxetine hydrobromide isopropanol solvate contains one molecule of isopropanol.

Figure 10:
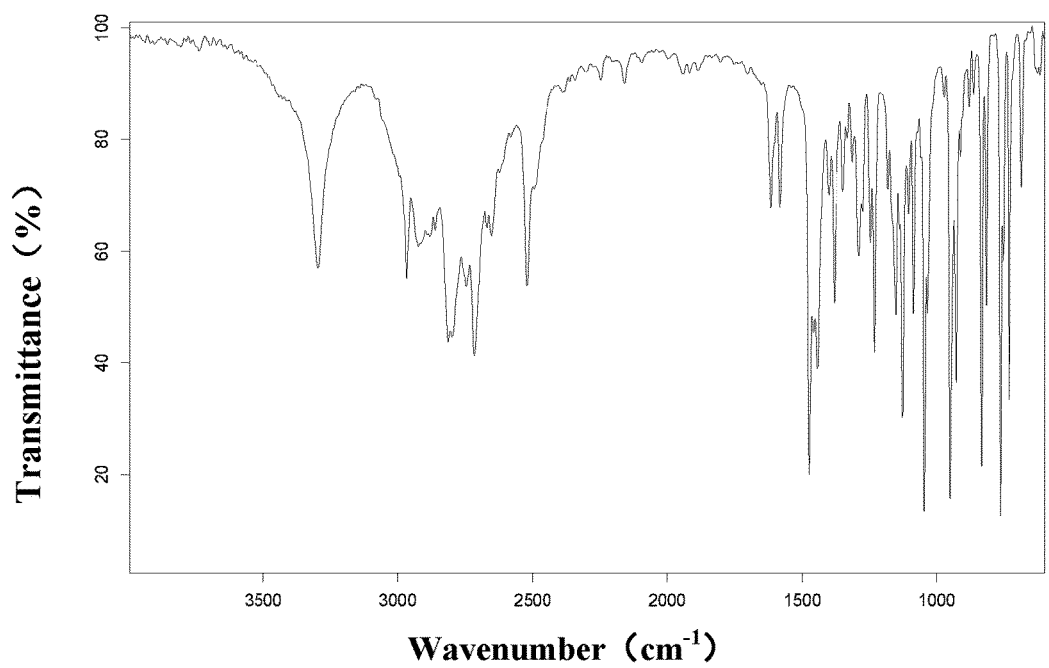
FIG. 10 is the IR spectrum of the crystal of the vortioxetine hydrobromide isopropanol solvate.

The IR spectrum is shown in FIG. 10.

Example 19

5.00 g (16.8 mmol) of vortioxetine was dissolved in 35 mL of isopropanol: water (5:1) mixed solution by sonication at 60° C. (the concentration of vortioxetine solution was 0.8 times of its solubility in isopropanol: water (5:1) at 60° C.); 4.05 g of hydrobromic acid (40% w/w, 20.0 mmol) was dissolved in 3 mL of isopropanol: water (4:1) mixed solution by sonication at 60° C. (the concentration of hydrobromic acid solution was 0.8 times of its solubility in isopropanol: water (4:1) at 60° C.); with stirring, the hydrobromic acid solution was slowly added dropwise to the vortioxetine solution; after completion of dropwise addition, the mixture was stirred for 15 min at 60° C. to produce a suspension; then the suspension was stirred at room temperature for 5 h and filtered; the filter cake was dried under vacuum at 30° C. for 18 h. The crystalline vortioxetine hydrobromide isopropanol solvate of the present invention was obtained. The yield was 6.92 g; the percent yield was 94.5%.

Example 20

5.00 g (16.8 mmol) of vortioxetine was dissolved in 80 mL of isopropanol by sonication at 50° C. (the concentration of vortioxetine solution in isopropanol was 0.5 times of its solubility in isopropanol at 50° C.); 5.06 g of hydrobromic acid (40% w/w, 25.0 mmol) was dissolved in 6 mL of isopropanol: water (2:1) mixed solution by sonication at 50° C. (the concentration of hydrobromic acid solution was 0.5 times of its solubility in isopropanol: water (2:1) mixed solution at 50° C.); with stirring, the hydrobromic acid solution was slowly added dropwise to the vortioxetine solution; after completion of dropwise addition, the mixture was stirred for 20 min at 50° C. to produce a suspension; then the suspension was stirred at room temperature for 10 h and filtered; the filter cake was dried under vacuum at 40° C. for 24 h. The crystalline vortioxetine hydrobromide isopropanol solvate of the present invention was obtained. The yield was 6.47 g; the percent yield was 88.3%.

Example 21

5.01 g (16.8 mmol) of vortioxetine was dissolved in 500 mL of isopropanol by sonication at 40° C. (the concentration of vortioxetine solution in isopropanol was 0.1 times of its solubility in isopropanol at 40° C.); 6.76 g of hydrobromic acid (40% w/w, 33.4 mmol) was dissolved in 18 mL of isopropanol by sonication at 40° C. (the concentration of hydrobromic acid solution in isopropanol was 0.1 times of its solubility in isopropanol at 40° C.); with stirring, the hydrobromic acid solution was slowly added dropwise to the vortioxetine solution; after completion of dropwise addition, the mixture was stirred for 30 min at 40° C. to produce a suspension; then the suspension was stirred at room temperature for 48 h and filtered; the filter cake was dried under vacuum at 10° C. for 48 h. The crystalline vortioxetine hydrobromide isopropanol solvate of the present invention was obtained. The yield was 5.68 g; the percent yield was 77.4%.

Example 22

To 10.00 g of vortioxetine hydrobromide prepared in preparation example 1, 50 mL of isopropanol was added to produce a suspension (the amount of vortioxetine hydrobromide in the suspension was 2 times of its solubility in the solvent at the crystallization temperature); the suspension was stirred at room temperature for 10 h and filtered; after drying at 40° C. for 10 h, the crystalline vortioxetine hydrobromide isopropanol solvate of the present invention was obtained. The yield was 11.02 g; the percent yield was 95.1%.

Example 23

To 15.00 g of vortioxetine hydrobromide prepared in preparation example 1, 50 mL of isopropanol: water (5:1) mixed solvent was added to produce a suspension (the amount of vortioxetine hydrobromide in the suspension was 3 times of its solubility in the mixed solvent at the crystallization temperature); the suspension was stirred at room temperature for 18 h and filtered; after drying at 30° C. for 18 h, the crystalline vortioxetine hydrobromide isopropanol solvate of the present invention was obtained. The yield was 16.32 g; the percent yield was 93.9%.

Example 24

To 24.00 g of vortioxetine hydrobromide prepared in preparation example 1, 50 mL of isopropanol: water (4:1) mixed solvent was added to produce a suspension (the amount of vortioxetine hydrobromide in the suspension was 5 times of its solubility in the mixed solvent at the crystallization temperature); the suspension was stirred at 40° C. for 24 h and filtered; after drying at 10° C. for 24 h, the crystalline vortioxetine hydrobromide isopropanol solvate of the present invention was obtained. The yield was 25.51 g; the percent yield was 91.7%.

Example 25

To 41.20 g of the β Form of vortioxetine hydrobromide prepared in preparation example 2, 50 mL of isopropanol: water (3:1) mixed solvent was added to produce a suspension (the amount of vortioxetine hydrobromide in the suspension was 8 times of its solubility in the mixed solvent at the crystallization temperature); the suspension was stirred at 45° C. for 32 h and filtered; after drying at 50° C. for 48 h, the crystalline vortioxetine hydrobromide isopropanol solvate of the present invention was obtained. The yield was 39.35 g; the percent yield was 82.4%.

Example 26

To 50.02 g of the β Form of vortioxetine hydrobromide prepared in preparation example 2, 50 mL of isopropanol: water (2:1) mixed solvent was added to produce a suspension (the amount of vortioxetine hydrobromide in the suspension was 10 times of its solubility in the mixed solvent at the crystallization temperature); the suspension was stirred at 50° C. for 48 h and filtered; after drying at 60° C. for 32 h, the crystalline vortioxetine hydrobromide isopropanol solvate of the present invention was obtained. The yield was 47.01 g; the percent yield was 81.1%.

The samples in examples 19 to 26 and the sample in example 18 have the same or similar XRPD patterns, TGA thermograms and IR spectra (not shown), indicating they are the same crystalline form.

Example 27

5.01 g (16.8 mmol) of vortioxetine was dissolved in 45 mL of ethyl acetate by sonication; 2.65 g of benzenesulfonic acid was dissolved in 14 mL of ethyl acetate by sonication; with stirring, the benzenesulfonic acid solution was slowly added dropwise to the vortioxetine solution; solids precipitated out during the dropwise-addition process; the solvent was removed by rotary evaporation at 50° C., then 20 ml of ethyl acetate was added, the resulting mixture was stirred for 10 min and filtered; after drying under vacuum at room temperature for 24 h, the vortioxetine besylate of the present invention was obtained. The yield was 7.21 g.

Example 28

10.02 g (33.6 mmol) of vortioxetine was dissolved in 60 mL of acetone by sonication; 5.28 g of benzenesulfonic acid was dissolved in 16 mL of acetone by sonication; with stirring, the benzenesulfonic acid solution was slowly added dropwise to the vortioxetine solution; solids precipitated out during the dropwise-addition process; the solvent was removed by rotary evaporation at 10° C., then 30 ml of acetone was added, the resulting mixture was stirred for 30 min and filtered; after drying under vacuum at 40° C. for 24 h, the vortioxetine besylate of the present invention was obtained. The yield was 13.80 g.

Example 29

5.02 g (16.8 mmol) of vortioxetine was dissolved in 80 mL of methanol by sonication; 2.65 g of benzenesulfonic acid was dissolved in 12 mL of methanol by sonication; with stirring, the benzenesulfonic acid solution was slowly added dropwise to the vortioxetine solution; solids precipitated out during the dropwise-addition process; after stirred at room temperature for 3 h, the mixture was filtered under reduced pressure; after drying under vacuum at 40° C. for 24 h, the crystalline form B of vortioxetine besylate of the present invention was obtained. The yield was 7.59 g.

The XRPD pattern of the crystalline form B of vortioxetine besylate has characteristic peaks at 2θ angles of 7.9±0.2°, 15.7±0.2°, 16.2±0.2°, 17.7±0.2°, 19.6±0.2° and 23.6±0.2°.

Example 30

5.00 g (16.8 mmol) of vortioxetine was dissolved in 80 mL of methanol by sonication; 4.06 g of benzenesulfonic acid was dissolved in 12 mL of methanol by sonication; with stirring, the benzenesulfonic acid solution was slowly added dropwise to the vortioxetine solution; solids precipitated out during the dropwise-addition process; after stirred at 40° C. for 1 h, the mixture was filtered under reduced pressure; after drying under vacuum at 40° C. for 24 h, the crystalline form B of vortioxetine besylate of the present invention was obtained. The yield was 7.02 g.

Example 31

5.41 g (18.1 mmol) of vortioxetine was dissolved in 350 mL of n-heptane by sonication; 5.70 g of benzenesulfonic acid was dissolved in 14 mL of n-heptane by sonication; with stirring, the benzenesulfonic acid solution was slowly added dropwise to the vortioxetine solution; solids precipitated out during the dropwise-addition process; after stirred at −10° C. for 10 h, the mixture was filtered under reduced pressure; after drying under vacuum at 40° C. for 24 h, the crystalline form B of vortioxetine besylate of the present invention was obtained. The yield was 6.12 g.

The samples prepared in examples 30 and 31 and the sample prepared in example 29 have the same or similar XRPD patterns.

Example 32

5.00 g (16.8 mmol) of vortioxetine was dissolved in 80 mL of methanol by sonication; 3.22 g of citric acid was dissolved in 14 mL of methanol by sonication; with stirring, the citric acid solution was slowly added dropwise to the vortioxetine solution; solids precipitated out during the dropwise-addition process; the solvent was removed by rotary evaporation at 50° C., then 20 ml of methanol was added, the resulting mixture was stirred for 10 min and filtered; after drying under vacuum at room temperature for 24 h, the vortioxetine citrate of the present invention was obtained. The yield was 8.11 g.

Example 33

5.01 g (16.8 mmol) of vortioxetine was dissolved in 30 mL of acetone by sonication; 4.10 g of citric acid was dissolved in 8 mL of acetone by sonication; with stirring, the citric acid solution was slowly added dropwise to the vortioxetine solution; solids precipitated out during the dropwise-addition process; the solvent was removed by rotary evaporation at 10° C., then 10 ml of acetone was added, the resulting mixture was stirred for 10 min and filtered; after drying under vacuum at 40° C. for 24 h, the vortioxetine citrate of the present invention was obtained. The yield was 8.12 g.

Example 34

5.33 g (17.8 mmol) of vortioxetine was dissolved in 90 mL of ethanol by sonication; 3.21 g of citric acid was dissolved in 12 mL of ethanol by sonication; with stirring, the citric acid solution was slowly added dropwise to the vortioxetine solution; solids precipitated out during the dropwise-addition process; after stirred at room temperature for 3 h, the mixture was filtered under reduced pressure; after drying under vacuum at 40° C. for 24 h, the crystalline form C of vortioxetine citrate of the present invention was obtained. The yield was 8.22 g.

The XRPD pattern of the crystalline form C of vortioxetine citrate has characteristic peaks at 2θ angles of 5.1±0.2°, 13.7±0.2°, 15.6±0.2°, 16.4±0.2°, 17.6±0.2° and 20.2±0.2°.

Example 35

5.00 g (16.8 mmol) of vortioxetine was dissolved in 100 mL of ethyl acetate by sonication; 5.3 g of citric acid was dissolved in 12 mL of ethyl acetate by sonication; with stirring, the citric acid solution was slowly added dropwise to the vortioxetine solution; solids precipitated out during the dropwise-addition process; after stirred at 30° C. for 4 h, the mixture was filtered under reduced pressure; after drying under vacuum at 40° C. for 24 h, the crystalline form C of vortioxetine citrate of the present invention was obtained. The yield was 7.96 g.

Example 36

5.01 g (16.8 mmol) of vortioxetine was dissolved in 200 mL of butanone by sonication; 6.4 g of citric acid was dissolved in 14 mL of butanone by sonication; with stirring, the citric acid solution was slowly added dropwise to the vortioxetine solution; solids precipitated out during the dropwise-addition process; after stirred at −10° C. for 10 h, the mixture was filtered under reduced pressure; after drying under vacuum at 40° C. for 24 h, the crystalline form C of vortioxetine citrate of the present invention was obtained. The yield was 6.20 g.

The samples prepared in examples 35 and 36 and the sample prepared in example 34 have the same or similar XRPD patterns.

Example 37

5.02 g (16.8 mmol) of vortioxetine was dissolved in 45 mL of methyl tert-butyl ether by sonication; 2.11 g of succinic acid was dissolved in 9 mL of methyl tert-butyl ether by sonication; with stirring, the succinic acid solution was slowly added dropwise to the vortioxetine solution; solids precipitated out during the dropwise-addition process; the solvent was removed by rotary evaporation at 10° C., then 50 ml of methyl tert-butyl ether was added, the resulting mixture was stirred for 30 min and filtered; after drying under vacuum at room temperature for 24 h, the vortioxetine succinate of the present invention was obtained. The yield was 6.81 g.

Example 38

5.02 g (16.8 mmol) of vortioxetine was dissolved in 90 mL of ethanol by sonication; 3.0 g of succinic acid was dissolved in 16 mL of ethanol by sonication; with stirring, the succinic acid solution was slowly added dropwise to the vortioxetine solution; solids precipitated out during the dropwise-addition process; the solvent was removed by rotary evaporation at 50° C., then 20 ml of ethanol was added, the resulting mixture was stirred for 40 min and filtered; after drying under vacuum at 40° C. for 24 h, the vortioxetine succinate of the present invention was obtained. The yield was 6.53 g.

Example 39

5.01 g (16.8 mmol) of vortioxetine was dissolved in 60 mL of isopropyl acetate by sonication; 3.21 g of succinic acid was dissolved in 10 mL of isopropyl acetate by sonication; with stirring, the succinic acid solution was slowly added dropwise to the vortioxetine solution; solids precipitated out during the dropwise-addition process; after stirred at room temperature for 3 h, the mixture was filtered under reduced pressure; after drying under vacuum at 40° C. for 24 h, the crystalline form S of vortioxetine succinate of the present invention was obtained. The yield was 6.74 g.

The XRPD pattern of the crystalline form S of vortioxetine succinate has characteristic peaks at 2θ angles of 5.0±0.2°, 11.4±0.2°, 13.5±0.2°, 18.2±0.2°, 20.7±0.2° and 27.2±0.2°.

Example 40

5.00 g (16.8 mmol) of vortioxetine was dissolved in 75 mL of methanol by sonication; 2.30 g of succinic acid was dissolved in 12 mL of methanol by sonication; with stirring, the succinic acid solution was slowly added dropwise to the vortioxetine solution; solids precipitated out during the dropwise-addition process; after stirred at 50° C. for 1 h, the mixture was filtered under reduced pressure; after drying under vacuum at 40° C. for 24 h, the crystalline form S of vortioxetine succinate of the present invention was obtained. The yield was 6.84 g.

Example 41

5.01 g (16.8 mmol) of vortioxetine was dissolved in 400 mL of n-heptane by sonication; 2.87 g of succinic acid was dissolved in 14 mL of n-heptane by sonication; with stirring, the succinic acid solution was slowly added dropwise to the vortioxetine solution; solids precipitated out during the dropwise-addition process; after stirred at room temperature for 10 h, the mixture was filtered under reduced pressure; after drying under vacuum at 40° C. for 24 h, the crystalline form S of vortioxetine succinate of the present invention was obtained. The yield was 6.02 g.

The samples prepared in examples 40 and 41 and the sample prepared in example 39 have the same or similar XRPD patterns.

Example 42

5.01 g (16.8 mmol) of vortioxetine was dissolved in 200 mL of butanone by sonication; 2.94 g of p-toluenesulfonic acid was dissolved in 16 mL of butanone by sonication; with stirring, the p-toluenesulfonic acid solution was slowly added dropwise to the vortioxetine solution; solids precipitated out during the dropwise-addition process; the solvent was removed by rotary evaporation at 10° C., then 40 ml of butanone was added, the resulting mixture was stirred for 10 min and filtered; after drying under vacuum at room temperature for 24 h, the vortioxetine p-toluenesulfonate of the present invention was obtained. The yield was 7.51 g.

Example 43

5.02 g (16.8 mmol) of vortioxetine was dissolved in 60 mL of ethyl acetate by sonication; 3.8 g of p-toluenesulfonic acid was dissolved in 10 mL of ethyl acetate by sonication; with stirring, the p-toluenesulfonic acid solution was slowly added dropwise to the vortioxetine solution; solids precipitated out during the dropwise-addition process; the solvent was removed by rotary evaporation at 50° C., then 40 ml of ethyl acetate was added, the resulting mixture was stirred for 20 min and filtered; after drying under vacuum at 40° C. for 24 h, the vortioxetine p-toluenesulfonate of the present invention was obtained. The yield was 7.33 g.

Example 44

5.03 g (16.8 mmol) of vortioxetine was dissolved in 75 mL of methanol by sonication; 3.79 g of p-toluenesulfonic acid was dissolved in 12 mL of methanol by sonication; with stirring, the p-toluenesulfonic acid solution was slowly added dropwise to the vortioxetine solution; solids precipitated out during the dropwise-addition process; after stirred at room temperature for 3 h, the mixture was filtered under reduced pressure; after drying under vacuum at 40° C. for 24 h, the crystalline form T of vortioxetine p-toluenesulfonate of the present invention was obtained. The yield was 7.59 g.

The XRPD pattern of the crystalline form T of vortioxetine p-toluenesulfonate has characteristic peaks at 2θ angles of 8.0±0.2°, 15.8±0.2°, 16.1±0.2°, 17.6±0.2°, 20.0±0.2° and 20.8±0.2°.

Example 45

5.00 g (16.8 mmol) of vortioxetine was dissolved in 300 mL of n-butanol by sonication; 3.71 g of p-toluenesulfonic acid was dissolved in 12 mL of n-butanol by sonication; with stirring, the p-toluenesulfonic acid solution was slowly added dropwise to the vortioxetine solution; solids precipitated out during the dropwise-addition process; after stirred at 45° C. for 1 h, the mixture was filtered under reduced pressure; after drying under vacuum at 40° C. for 24 h, the crystalline form T of vortioxetine p-toluenesulfonate of the present invention was obtained. The yield was 6.30 g.

Example 46

5.01 g (16.8 mmol) of vortioxetine was dissolved in 350 mL of methyl tert-butyl ether by sonication; 5.74 g of p-toluenesulfonic acid was dissolved in 18 mL of methyl tert-butyl ether by sonication; with stirring, the p-toluenesulfonic acid solution was slowly added dropwise to the vortioxetine solution; solids precipitated out during the dropwise-addition process; after stirred at −10° C. for 10 h, the mixture was filtered under reduced pressure; after drying under vacuum at 40° C. for 24 h, the crystalline form T of vortioxetine p-toluenesulfonate of the present invention was obtained. The yield was 6.02 g.

The samples prepared in examples 45 and 46 and the sample prepared in example 44 have the same or similar XRPD patterns.

Example 47

5.01 g (16.8 mmol) of vortioxetine was dissolved in 75 mL of methanol by sonication; 3.97 g of p-chlorobenzenesulfonic acid was dissolved in 16 mL of methanol by sonication; with stirring, the p-chlorobenzenesulfonic acid solution was slowly added dropwise to the vortioxetine solution; solids precipitated out during the dropwise-addition process; the solvent was removed by rotary evaporation at 10° C., then 40 ml of methanol was added, the resulting mixture was stirred for 10 min and filtered; after drying under vacuum at room temperature for 24 h, the vortioxetine p-chlorobenzenesulfonate of the present invention was obtained. The yield was 7.89 g.

Example 48

5.02 g (16.8 mmol) of vortioxetine was dissolved in 150 mL of ethanol by sonication; 4.00 g of p-chlorobenzenesulfonic acid was dissolved in 10 mL of ethanol by sonication; with stirring, the p-chlorobenzenesulfonic acid solution was slowly added dropwise to the vortioxetine solution; solids precipitated out during the dropwise-addition process; the solvent was removed by rotary evaporation at 50° C., then 40 ml of ethanol was added, the resulting mixture was stirred for 20 min and filtered; after drying under vacuum at 40° C. for 24 h, the vortioxetine p-chlorobenzenesulfonate of the present invention was obtained. The yield was 7.60 g.

Example 49

5.03 g (16.8 mmol) of vortioxetine was dissolved in 100 mL of acetone by sonication; 3.22 g of p-chlorobenzenesulfonic acid was dissolved in 12 mL of acetone by sonication; with stirring, the p-chlorobenzenesulfonic acid solution was slowly added dropwise to the vortioxetine solution; solids precipitated out during the dropwise-addition process; after stirred at room temperature for 3 h, the mixture was filtered under reduced pressure; after drying under vacuum at 40° C. for 24 h, the crystalline form Ch of vortioxetine p-chlorobenzenesulfonate of the present invention was obtained. The yield was 7.01 g.

The XRPD pattern of the crystalline form Ch of vortioxetine p-chlorobenzenesulfonate has characteristic peaks at 2θ angles of 15.7±0.2°, 16.2±0.2°, 17.7±0.2°, 20.0±0.2°, 22.7±0.2° and 23.1±0.2°.

Example 50

5.00 g (16.8 mmol) of vortioxetine was dissolved in 450 mL of ethyl acetate by sonication; 5.01 g of p-chlorobenzenesulfonic acid was dissolved in 10 mL of ethyl acetate by sonication; with stirring, the p-chlorobenzenesulfonic acid solution was slowly added dropwise to the vortioxetine solution; solids precipitated out during the dropwise-addition process; after stirred at 30° C. for 1 h, the mixture was filtered under reduced pressure; after drying under vacuum at 40° C. for 24 h, the crystalline form Ch of vortioxetine p-chlorobenzenesulfonate of the present invention was obtained. The yield was 6.11 g.

Example 51

5.01 g (16.8 mmol) of vortioxetine was dissolved in 80 mL of isopropanol by sonication; 6.43 g of p-chlorobenzenesulfonic acid was dissolved in 18 mL of isopropanol by sonication; with stirring, the p-chlorobenzenesulfonic acid solution was slowly added dropwise to the vortioxetine solution; solids precipitated out during the dropwise-addition process; after stirred at −10° C. for 10 h, the mixture was filtered under reduced pressure; after drying under vacuum at 40° C. for 24 h, the crystalline form Ch of vortioxetine p-chlorobenzenesulfonate of the present invention was obtained. The yield was 6.98 g.

The samples prepared in examples 50 and 51 and the sample prepared in example 49 have the same or similar XRPD patterns.

Example 52

5.01 g (16.8 mmol) of vortioxetine was dissolved in 75 mL of ethanol by sonication; 4.26 g of ethanedisulfonic acid was dissolved in 16 mL of ethanol by sonication; with stirring, the ethanedisulfonic acid solution was slowly added dropwise to the vortioxetine solution; solids precipitated out during the dropwise-addition process; the solvent was removed by rotary evaporation at 10° C., then 40 ml of ethanol was added, the resulting mixture was stirred for 10 min and filtered; after drying under vacuum at room temperature for 24 h, the vortioxetine ethanedisulfonate of the present invention was obtained. The yield was 7.90 g.

Example 53

5.02 g (16.8 mmol) of vortioxetine was dissolved in 150 mL of n-butanol by sonication; 5.01 g of ethanedisulfonic acid was dissolved in 10 mL of n-butanol by sonication; with stirring, the ethanedisulfonic acid solution was slowly added dropwise to the vortioxetine solution; solids precipitated out during the dropwise-addition process; the solvent was removed by rotary evaporation at 50° C., then 40 ml of n-butanol was added, the resulting mixture was stirred for 20 min and filtered; after drying under vacuum at 40° C. for 24 h, the vortioxetine ethanedisulfonate of the present invention was obtained. The yield was 7.65 g.

Example 54

5.03 g (16.8 mmol) of vortioxetine was dissolved in 90 mL of isopropyl acetate by sonication; 4.00 g of ethanedisulfonic acid was dissolved in 12 mL of isopropyl acetate by sonication; with stirring, the ethanedisulfonic acid solution was slowly added dropwise to the vortioxetine solution; solids precipitated out during the dropwise-addition process; after stirred at room temperature for 3 h, the mixture was filtered under reduced pressure; after drying under vacuum at 40° C. for 24 h, the crystalline form E of vortioxetine ethanedisulfonate of the present invention was obtained. The yield was 7.23 g.

The XRPD pattern of the crystalline form E of vortioxetine ethanedisulfonate has characteristic peaks at 2θ angles of 3.7±0.2°, 4.4±0.2°, 16.9±0.2°, 18.7±0.2°, 19.7±0.2° and 20.4±0.2°.

Example 55

5.00 g (16.8 mmol) of vortioxetine was dissolved in 150 mL of acetone by sonication; 3.33 g of ethanedisulfonic acid was dissolved in 10 mL of acetone by sonication; with stirring, the ethanedisulfonic acid solution was slowly added dropwise to the vortioxetine solution; solids precipitated out during the dropwise-addition process; after stirred at 40° C. for 1 h, the mixture was filtered under reduced pressure; after drying under vacuum at 40° C. for 24 h, the crystalline form E of vortioxetine ethanedisulfonate of the present invention was obtained. The yield was 6.79 g.

Example 56

5.01 g (16.8 mmol) of vortioxetine was dissolved in 200 mL of butanone by sonication; 3.45 g of ethanedisulfonic acid was dissolved in 15 mL of butanone by sonication; with stirring, the ethanedisulfonic acid solution was slowly added dropwise to the vortioxetine solution; solids precipitated out during the dropwise-addition process; after stirred at 20° C. for 10 h, the mixture was filtered under reduced pressure; after drying under vacuum at 40° C. for 24 h, the crystalline form E of vortioxetine ethanedisulfonate of the present invention was obtained. The yield was 6.29 g.

The samples prepared in examples 55 and 56 and the sample prepared in example 54 have the same or similar XRPD patterns.

Example 57

5.01 g (16.8 mmol) of vortioxetine was dissolved in 100 mL of methyl tert-butyl ether by sonication; 2.67 g of α-ketoglutaric acid was dissolved in 16 mL of methyl tert-butyl ether by sonication; with stirring, the α-ketoglutaric acid solution was slowly added dropwise to the vortioxetine solution; solids precipitated out during the dropwise-addition process; the solvent was removed by rotary evaporation at 10° C., then 40 ml of methyl tert-butyl ether was added, the resulting mixture was stirred for 10 min and filtered; after drying under vacuum at room temperature for 24 h, the vortioxetine α-ketoglutarate of the present invention was obtained. The yield was 7.32 g.

Example 58

5.00 g (16.8 mmol) of vortioxetine was dissolved in 380 mL of n-butanol by sonication; 2.50 g of α-ketoglutaric acid was dissolved in 10 mL of n-butanol by sonication; with stirring, the α-ketoglutaric acid solution was slowly added dropwise to the vortioxetine solution; solids precipitated out during the dropwise-addition process; the solvent was removed by rotary evaporation at 50° C., then 40 ml of n-butanol was added, the resulting mixture was stirred for 20 min and filtered; after drying under vacuum at 40° C. for 24 h, the vortioxetine α-ketoglutarate of the present invention was obtained. The yield was 6.89 g.

Example 59

5.03 g (16.8 mmol) of vortioxetine was dissolved in 60 mL of ethyl acetate by sonication; 3.34 g of α-ketoglutaric acid was dissolved in 12 mL of ethyl acetate by sonication; with stirring, the α-ketoglutaric acid solution was slowly added dropwise to the vortioxetine solution; solids precipitated out during the dropwise-addition process; after stirred at room temperature for 5 h, the mixture was filtered under reduced pressure; after drying under vacuum at 40° C. for 24 h, the crystalline form G of vortioxetine α-ketoglutarate of the present invention was obtained. The yield was 6.74 g.

The XRPD pattern of the crystalline form G of vortioxetine α-ketoglutarate has characteristic peaks at 2θ angles of 4.4±0.2°, 11.3±0.2°, 12.8±0.2°, 16.5±0.2°, 20.8±0.2° and 21.4±0.2°.

Example 60

5.00 g (16.8 mmol) of vortioxetine was dissolved in 150 mL of acetone by sonication; 3.02 g of α-ketoglutaric acid was dissolved in 10 mL of acetone by sonication; with stirring, the α-ketoglutaric acid solution was slowly added dropwise to the vortioxetine solution; solids precipitated out during the dropwise-addition process; after stirred at 35° C. for 1 h, the mixture was filtered under reduced pressure; after drying under vacuum at 40° C. for 24 h, the crystalline form G of vortioxetine α-ketoglutarate of the present invention was obtained. The yield was 6.25 g.

Example 61

5.01 g (16.8 mmol) of vortioxetine was dissolved in 380 mL of n-heptane by sonication; 4.87 g of α-ketoglutaric acid was dissolved in 15 mL of n-heptane by sonication; with stirring, the α-ketoglutaric acid solution was slowly added dropwise to the vortioxetine solution; solids precipitated out during the dropwise-addition process; after stirred at −10° C. for 48 h, the mixture was filtered under reduced pressure; after drying under vacuum at 40° C. for 24 h, the crystalline form G of vortioxetine α-ketoglutarate of the present invention was obtained. The yield was 6.11 g.

The samples prepared in examples 60 and 61 and the sample prepared in example 59 have the same or similar XRPD patterns.

Example 62

5.01 g (16.8 mmol) of vortioxetine was dissolved in 75 mL of methanol by sonication; 6.12 g of 1,5-naphthalene disulfonic acid was dissolved in 16 mL of methanol by sonication; with stirring, the 1,5-naphthalene disulfonic acid solution was slowly added dropwise to the vortioxetine solution; solids precipitated out during the dropwise-addition process; the solvent was removed by rotary evaporation at 10° C., then 20 ml of methanol was added, the resulting mixture was stirred for 10 min and filtered; after drying under vacuum at room temperature for 24 h, the vortioxetine 1,5-naphthalenedisulfonate of the present invention was obtained. The yield was 11.01 g.

Example 63

5.02 g (16.8 mmol) of vortioxetine was dissolved in 150 mL of isopropanol by sonication; 4.18 g of 1,5-naphthalene disulfonic acid was dissolved in 15 mL of isopropanol by sonication; with stirring, the 1,5-naphthalene disulfonic acid solution was slowly added dropwise to the vortioxetine solution;

solids precipitated out during the dropwise-addition process; the solvent was removed by rotary evaporation at 50° C., then 40 ml of isopropanol was added, the mixture was stirred for 20 min and filtered; after drying under vacuum at 40° C. for 24 h, the vortioxetine 1,5-naphthalenedisulfonate of the present invention was obtained. The yield was 10.55 g.

Example 64

5.01 g (16.8 mmol) of vortioxetine was dissolved in 60 mL of butanone by sonication; 5.57 g of 1,5-naphthalene disulfonic acid was dissolved in 12 mL of butanone by sonication; with stirring, the 1,5-naphthalene disulfonic acid solution was slowly added dropwise to the vortioxetine solution; solids precipitated out during the dropwise-addition process; after stirred at room temperature for 5 h, the mixture was filtered under reduced pressure; after drying under vacuum at 40° C. for 24 h, the crystalline form N of vortioxetine 1,5-naphthalenedisulfonate of the present invention was obtained. The yield was 10.49 g.

The XRPD pattern of the crystalline form N of vortioxetine 1,5-napadisilate has characteristic peaks at 2θ angles of 13.1±0.2°, 14.4±0.2°, 15.9±0.2°, 18.0±0.2°, 18.9±0.2° and 23.4±0.2°.

Example 65

5.00 g (16.8 mmol) of vortioxetine was dissolved in 450 mL of ethyl acetate by sonication; 8.01 g of 1,5-naphthalene disulfonic acid was dissolved in 10 mL of ethyl acetate by sonication; with stirring, the 1,5-naphthalene disulfonic acid solution was slowly added dropwise to the vortioxetine solution; solids precipitated out during the dropwise-addition process; after stirred at 40° C. for 1 h, the mixture was filtered under reduced pressure; after drying under vacuum at 40° C. for 24 h, the crystalline form N of vortioxetine 1,5-naphthalenedisulfonate of the present invention was obtained. The yield was 9.87 g.

Example 66

5.01 g (16.8 mmol) of vortioxetine was dissolved in 380 mL of n-heptane by sonication; 9.11 g of 1,5-naphthalene disulfonic acid was dissolved in 18 mL of n-heptane by sonication; with stirring, the 1,5-naphthalene disulfonic acid solution was slowly added dropwise to the vortioxetine solution; solids precipitated out during the dropwise-addition process; after stirred at 20° C. for 7 h, the mixture was filtered under reduced pressure; after drying under vacuum at 40° C. for 24 h, the crystalline form N of vortioxetine 1,5-naphthalenedisulfonate of the present invention was obtained. The yield was 10.06 g.

The samples prepared in examples 65 and 66 and the sample prepared in example 64 have the same or similar XRPD patterns.

Example 67

5.01 g (16.8 mmol) of vortioxetine was dissolved in 100 mL of methyl tert-butyl ether by sonication; 4.10 g of 2-naphthalene sulfonic acid was dissolved in 16 mL of methyl tert-butyl ether by sonication; with stirring, the 2-naphthalene sulfonic acid solution was slowly added dropwise to the vortioxetine solution; solids precipitated out during the dropwise-addition process; the solvent was removed by rotary evaporation at 10° C., then 40 ml of methyl tert-butyl ether was added, the mixture was stirred for 10 min and filtered; after drying under vacuum at room temperature for 24 h, the vortioxetine 2-naphthalenesulfonate of the present invention was obtained. The yield was 8.42 g.

Example 68

5.00 g (16.8 mmol) of vortioxetine was dissolved in 150 mL of n-butanol by sonication; 6.13 g of 2-naphthalene sulfonic acid was dissolved in 10 mL of n-butanol by sonication; with stirring, the 2-naphthalene sulfonic acid solution was slowly added dropwise to the vortioxetine solution; solids precipitated out during the dropwise-addition process; the solvent was removed by rotary evaporation at 50° C., then 30 ml of n-butanol was added, the resulting mixture was stirred for 20 min and filtered; after drying under vacuum at 40° C. for 24 h, the vortioxetine 2-naphthalenesulfonate of the present invention was obtained. The yield was 8.30 g.

Example 69

5.03 g (16.8 mmol) of vortioxetine was dissolved in 60 mL of ethyl acetate by sonication; 3.48 g of 2-naphthalene sulfonic acid was dissolved in 12 mL of ethyl acetate by sonication; with stirring, the 2-naphthalene sulfonic acid solution was slowly added dropwise to the vortioxetine solution; solids precipitated out during the dropwise-addition process; after stirred at room temperature for 3 h, the mixture was filtered under reduced pressure; after drying under vacuum at 40° C. for 24 h, the crystalline form Na of vortioxetine 2-naphthalenesulfonate of the present invention was obtained. The yield was 8.36 g.

The XRPD pattern of the crystalline form Na of vortioxetine 2-naphthalenesulfonate in the present invention has characteristic peaks at 2θ angles of 6.4±0.2°, 12.7±0.2°, 18.6±0.2°, 19.7±0.2°, 20.0±0.2° and 24.4±0.2°.

Example 70

5.00 g (16.8 mmol) of vortioxetine was dissolved in 150 mL of acetone by sonication; 4.18 g of 2-naphthalene sulfonic acid was dissolved in 10 mL of acetone by sonication; with stirring, the 2-naphthalene sulfonic acid solution was slowly added dropwise to the vortioxetine solution; solids precipitated out during the dropwise-addition process; after stirred at 30° C. for 1 h, the mixture was filtered under reduced pressure; after drying under vacuum at 40° C. for 24 h, the crystalline form Na of vortioxetine 2-naphthalenesulfonate of the present invention was obtained. The yield was 8.01 g.

Example 71

5.01 g (16.8 mmol) of vortioxetine was dissolved in 450 mL of ethyl acetone by sonication; 4.01 g of 2-naphthalene sulfonic acid was dissolved in 15 mL of ethyl acetone by sonication; with stirring, the 2-naphthalene sulfonic acid solution was slowly added dropwise to the vortioxetine solution; solids precipitated out during the dropwise-addition process; after stirred at 10° C. for 16 h, the mixture was filtered under reduced pressure; after drying under vacuum at 40° C. for 24 h, the crystalline form Na of vortioxetine 2-naphthalenesulfonate of the present invention was obtained. The yield was 7.84 g.

The samples prepared in examples 70 and 71 and the sample prepared in example 69 have the same or similar XRPD patterns.

Example 72

5.01 g (16.8 mmol) of vortioxetine was dissolved in 75 mL of ethanol by sonication; 3.45 g of 3-hydroxy-2-naphthoic acid was dissolved in 16 mL of ethanol by sonication; with stirring, the 3-hydroxy-2-naphthoic acid solution was slowly added dropwise to the vortioxetine solution; solids precipitated out during the dropwise-addition process; the solvent was removed by rotary evaporation at 10° C., then 40 ml of ethanol was added, the resulting mixture was stirred for 10 min and filtered; after drying under vacuum at room temperature for 24 h, the vortioxetine 3-hydroxy-2-naphthoate of the present invention was obtained. The yield was 6.90 g.

Example 73

5.02 g (16.8 mmol) of vortioxetine was dissolved in 200 mL of methyl tert-butyl ether by sonication; 6.01 g of 3-hydroxy-2-naphthoic acid was dissolved in 10 mL of methyl tert-butyl ether by sonication; with stirring, the 3-hydroxy-2-naphthoic acid solution was slowly added dropwise to the vortioxetine solution; solids precipitated out during the dropwise-addition process; the solvent was removed by rotary evaporation at 50° C., then 40 ml of methyl tert-butyl ether was added, the resulting mixture was stirred for 20 min and filtered; after drying under vacuum at 40° C. for 24 h, the vortioxetine 3-hydroxy-2-naphthoate of the present invention was obtained. The yield was 6.71 g.

Example 74

5.02 g (16.8 mmol) of vortioxetine was dissolved in 450 mL of isopropyl acetate by sonication; 3.15 g of 3-hydroxy-2-naphthoic acid was dissolved in 12 mL of isopropyl acetate by sonication; with stirring, the 3-hydroxy-2-naphthoic acid solution was slowly added dropwise to the vortioxetine solution; solids precipitated out during the dropwise-addition process; after stirred at room temperature for 3 h, the mixture was filtered under reduced pressure; after drying under vacuum at 40° C. for 24 h, the crystalline form H of vortioxetine 3-hydroxy-2-naphthoate of the present invention was obtained. The yield was 6.29 g.

The XRPD pattern of the crystalline form H of vortioxetine 3-hydroxy-2-naphthoate in the present invention has characteristic peaks at 2θ angles of 11.8±0.2°, 15.2±0.2°, 16.9±0.2°, 17.8±0.2°, 18.5±0.2° and 21.4±0.2°.

Example 75

5.00 g (16.8 mmol) of vortioxetine was dissolved in 80 mL of acetone by sonication; 5.00 g of 3-hydroxy-2-naphthoic acid was dissolved in 10 mL of acetone by sonication; with stirring, the 3-hydroxy-2-naphthoic acid solution was slowly added dropwise to the vortioxetine solution; solids precipitated out during the dropwise-addition process; after stirred at 30° C. for 1 h, the mixture was filtered under reduced pressure; after drying under vacuum at 40° C. for 24 h, the crystalline form H of vortioxetine 3-hydroxy-2-naphthoate of the present invention was obtained. The yield was 6.59 g.

Example 76

5.01 g (16.8 mmol) of vortioxetine was dissolved in 500 mL of n-heptane by sonication; 6.28 g of 3-hydroxy-2-naphthoic acid was dissolved in 15 mL of n-heptane by sonication; with stirring, the 3-hydroxy-2-naphthoic acid solution was slowly added dropwise to the vortioxetine solution; solids precipitated out during the dropwise-addition process; after stirred at 5° C. for 10 h, the mixture was filtered under reduced pressure; after drying under vacuum at 40° C. for 24 h, the crystalline form H of vortioxetine 3-hydroxy-2-naphthoate of the present invention was obtained. The yield was 6.21 g.

The samples prepared in examples 75 and 76 and the sample prepared in example 74 have the same or similar XRPD patterns.

Example 77

5.01 g (16.8 mmol) of vortioxetine was dissolved in 75 mL of ethanol by sonication; 3.45 g of 1-hydroxy-2-naphthoic acid was dissolved in 16 mL of ethanol by sonication; with stirring, the 1-hydroxy-2-naphthoic acid solution was slowly added dropwise to the vortioxetine solution; solids precipitated out during the dropwise-addition process; the solvent was removed by rotary evaporation at 10° C., then 40 ml of ethanol was added, the resulting mixture was stirred for 10 min and filtered; after drying under vacuum at room temperature for 24 h, the vortioxetine 1-hydroxy-2-naphthoate of the present invention was obtained. The yield was 6.91 g.

Example 78

5.02 g (16.8 mmol) of vortioxetine was dissolved in 60 mL of butanone by sonication; 4.16 g of 1-hydroxy-2-naphthoic acid was dissolved in 10 mL of butanone by sonication; with stirring, the 1-hydroxy-2-naphthoic acid solution was slowly added dropwise to the vortioxetine solution; solids precipitated out during the dropwise-addition process; the solvent was removed by rotary evaporation at 31° C., then 40 ml of butanone was added, the resulting mixture was stirred for 20 min and filtered; after drying under vacuum at 40° C. for 24 h, the vortioxetine 1-hydroxy-2-naphthoate of the present invention was obtained. The yield was 6.80 g.

Example 79

5.03 g (16.8 mmol) of vortioxetine was dissolved in 450 mL of isopropyl acetate by sonication; 3.23 g of 1-hydroxy-2-naphthoic acid was dissolved in 12 mL of isopropyl acetate by sonication; with stirring, the 1-hydroxy-2-naphthoic acid solution was slowly added dropwise to the vortioxetine solution; solids precipitated out during the dropwise-addition process; after stirred at room temperature for 4 h, the mixture was filtered under reduced pressure; after drying under vacuum at 40° C. for 24 h, the crystalline form Hy of vortioxetine 1-hydroxy-2-naphthoate of the present invention was obtained. The yield was 6.52 g.

The XRPD pattern of the crystalline form Hy of vortioxetine 1-hydroxy-2-naphthoate in the present invention has characteristic peaks at 2θ angles of 6.1±0.2°, 7.2±0.2°, 11.2±0.2°, 14.3±0.2°, 18.9±0.2° and 22.4±0.2°.

Example 80

5.00 g (16.8 mmol) of vortioxetine was dissolved in 250 mL of methyl tert-butyl ether by sonication; 4.01 g of 1-hydroxy-2-naphthoic acid was dissolved in 10 mL of methyl tert-butyl ether by sonication; with stirring, the 1-hydroxy-2-naphthoic acid solution was slowly added dropwise to the vortioxetine solution; solids precipitated out during the dropwise-addition process; after stirred at 40° C. for 1 h, the mixture was filtered under reduced pressure; after drying under vacuum at 40° C. for 24 h, the crystalline form Hy of vortioxetine 1-hydroxy-2-naphthoate of the present invention was obtained. The yield was 6.48 g.

Example 81

5.01 g (16.8 mmol) of vortioxetine was dissolved in 500 mL of n-heptane by sonication; 4.81 g of 1-hydroxy-2-naphthoic acid was dissolved in 15 mL of n-heptane by sonication; with stirring, the 1-hydroxy-2-naphthoic acid solution was slowly added dropwise to the vortioxetine solution; solids precipitated out during the dropwise-addition process; after stirred at 10° C. for 36 h, the mixture was filtered under reduced pressure; after drying under vacuum at 40° C. for 24 h, the crystalline form Hy of vortioxetine 1-hydroxy-2-naphthoate of the present invention was obtained. The yield was 6.39 g.

The samples prepared in examples 80 and 81 and the sample prepared in example 79 have the same or similar XRPD patterns.

Example 82

5.01 g (16.8 mmol) of vortioxetine was dissolved in 75 mL of ethanol by sonication; 2.18 g of oxalic acid was dissolved in 16 mL of ethanol by sonication; with stirring, the oxalic acid solution was slowly added dropwise to the vortioxetine solution; solids precipitated out during the dropwise-addition process; the solvent was removed by rotary evaporation at 10° C., then 40 ml of ethanol was added, the resulting mixture was stirred for 10 min and filtered; after drying under vacuum at room temperature for 24 h, the vortioxetine oxalate of the present invention was obtained. The yield was 6.51 g.

Example 83

5.02 g (16.8 mmol) of vortioxetine was dissolved in 150 mL of isopropanol by sonication; 1.77 g of oxalic acid was dissolved in 10 mL of isopropanol by sonication; with stirring, the oxalic acid solution was slowly added dropwise to the vortioxetine solution; solids precipitated out during the dropwise-addition process; the solvent was removed by rotary evaporation at 50° C., then 40 ml of isopropanol was added, the resulting mixture was stirred for 25 min and filtered; after drying under vacuum at 40° C. for 24 h, the vortioxetine oxalate of the present invention was obtained. The yield was 6.51 g.

Example 84

5.03 g (16.8 mmol) of vortioxetine was dissolved in 450 mL of isopropyl acetate by sonication; 2.36 g of oxalic acid was dissolved in 12 mL of isopropyl acetate by sonication;

with stirring, the oxalic acid solution was slowly added dropwise to the vortioxetine solution; solids precipitated out during the dropwise-addition process; after stirred at room temperature for 3 h, the mixture was filtered under reduced pressure; after drying under vacuum at 40° C. for 24 h, the crystalline form O of vortioxetine oxalate of the present invention was obtained. The yield was 6.33 g.

The XRPD pattern of the crystalline form O of vortioxetine oxalate in the present invention has characteristic peaks at 2θ angles of 3.6±0.2°, 10.4±0.2°, 11.9±0.2°, 14.7±0.2°, 19.2±0.2° and 20.7±0.2°.

Example 85

5.00 g (16.8 mmol) of vortioxetine was dissolved in 100 mL of acetone by sonication; 1.51 g of oxalic acid was dissolved in 10 mL of acetone by sonication; with stirring, the oxalic acid solution was slowly added dropwise to the vortioxetine solution; solids precipitated out during the dropwise-addition process; after stirred at 32° C. for 1 h, the mixture was filtered under reduced pressure; after drying under vacuum at 40° C. for 24 h, the crystalline form O of vortioxetine oxalate of the present invention was obtained. The yield was 6.31 g.

Example 86

5.01 g (16.8 mmol) of vortioxetine was dissolved in 200 mL of methyl tert-butyl ether by sonication; 2.20 g of oxalic acid was dissolved in 15 mL of methyl tert-butyl ether by sonication; with stirring, the oxalic acid solution was slowly added dropwise to the vortioxetine solution; solids precipitated out during the dropwise-addition process; after stirred at 8° C. for 10 h, the mixture was filtered under reduced pressure; after drying under vacuum at 40° C. for 24 h, the crystalline form O of vortioxetine oxalate of the present invention was obtained. The yield was 6.21 g.

The samples prepared in examples 85 and 86 and the sample prepared in example 84 have the same or similar XRPD patterns.

Example 87

12.5 g of the crystals of the vortioxetine hydrobromide isopropanol solvate of the present invention prepared in example 22 were dried under vacuum at 70° C. for 24 h; after removal of the solvent, 10.8 g of vortioxetine hydrobromide was obtained.

Example 88

The crystalline vortioxetine hemihydrobromide form of the present invention and the known β Form of vortioxetine hydrobromide were subjected to stability competition test and hygroscopicity comparison. See Table 2 for the results.

Stability competition test: An equal quantity (250 mg) of the crystalline vortioxetine hemihydrobromide form of the present invention prepared in example 4 and the β Form of vortioxetine hydrobromide prepared in preparation example 2 were respectively added to 3 mL of ethanol or water to produce suspensions. No solvate was formed in ethanol or water. The suspensions were slurried for 7 days at room temperature or at 60° C., and then XRPD characterization analyses were performed.

Hygroscopicity comparison: DVS isothermal sorption curves were used, and weight changes within the 20%-80% RH range were measured.

TABLE 2

Comparison of the crystalline form of the present invention and the known crystalline form

| Crystalline Form | Stability Competition Test | Hygroscopicity Comparison |
|---|---|---|
| the known β Form of vortioxetine hydrobromide | ①At room temperature, in competitive slurry of the known β Form of vortioxetine hydrobromide and the vortioxetine hemihydrobromide crystalline form of the present invention in ethanol or water; the known β Form of vortioxetine hydrobromide transformed into the vortioxetine hemihydrobromide crystalline form of the present invention, while the vortioxetine hemihydrobromide crystalline form of the present invention kept unchanged". ②At 60° C., in competitive slurry of the known β Form of vortioxetine hydrobromide and the vortioxetine hemihydrobromide crystalline form of the present invention in ethanol or water, and the known β Form of vortioxetine hydrobromide transformed into the vortioxetine hemihydrobromide crystalline form of the present invention, while the vortioxetine hemihydrobromide crystalline form of the present invention kept unchanged". | 0.60% |
| the vortioxetine hemihydrobromide crystalline form of the present invention | | 0.28% |

It can be known from results in Table 2 that: At room temperature or at 60° C., in competitive slurry of the known β Form of vortioxetine hydrobromide and the vortioxetine hemihydrobromide crystalline form of the present invention in ethanol or water, XRPD showed the known β Form of vortioxetine hydrobromide completely transformed into the vortioxetine hemihydrobromide crystalline form of the present invention, while the vortioxetine hemihydrobromide crystalline form of the present invention kept unchanged, indicating that the vortioxetine hemihydrobromide crystalline form of the present invention is more stable than the known β Form of vortioxetine hydrobromide. According to hygroscopicity comparison within the relative humidity range of 20%-80%, the vortioxetine hemihydrobromide crystalline form of the present invention is less hygroscopic than the known β Form of vortioxetine hydrobromide.

Example 89

The vortioxetine hydrobromide isopropanol solvate of the present invention, vortioxetine hydrobromide transformed from the vortioxetine hydrobromide isopropanol solvate of the present invention and the known vortioxetine hydrobromide were compared in terms of the HPLC purity.

The detailed operation is as follows:

By reference to preparation example 1, two batches of samples of the known vortioxetine hydrobromide were prepared, numbered as 1 and 2, respectively;

By reference to example 22, using the above samples 1 and 2 as the raw materials, the crystalline form of the vortioxetine hydrobromide isopropanol solvate of the present invention was prepared, and the two batches of products were numbered as 3 and 4, respectively.

By reference to example 87, the above samples 3 and 4 were transformed to the known vortioxetine hydrobromide, and the two batches of products were numbered as 5 and 6, respectively.

Respectively, about 5 mg of the samples 1 to 6 were subjected to HPLC purity analysis. See Table 3 for the results.

TABLE 3

Results of the HPLC purity analysis

| Sample No. | Maximum individual impurity content (area %) | Sample purity (area %) |
| --- | --- | --- |
| 1 | 0.37 | 99.63 |
| 2 | 0.19 | 99.71 |
| 3 | Not detected | 100.0 |
| 4 | Not detected | 100.0 |
| 5 | Not detected | 100.0 |
| 6 | Not detected | 100.0 |

Table 3 shows that the purity of the known vortioxetine hydrobromide was lower, and its maximum individual impurity content was higher; was the vortioxetine hydrobromide isopropanol solvate of the present invention was prepared from the known vortioxetine hydrobromide, and then it was used to prepared the known vortioxetine hydrobromide, no impurity was detected, and its purity is 100%; i.e., a high-quality product was obtained. These results indicate that the maximum individual impurity in samples of the known vortioxetine hydrobromide can be removed through formation of the vortioxetine hydrobromide isopropanol solvate of the present invention; i.e. formation of the isopropanol solvate could acts as a purification process.

Example 90

Capsules were prepared with the crystalline form of vortioxetine hemihydrobromide of the present invention as the active pharmaceutical ingredient. The strength was 150 mg/capsule containing 11.3 mg of the vortioxetine hemihydrobromide (equivalent to 10 mg of vortioxetine). See Table 4 for the detailed formula.

TABLE 4

Formula of capsules (10 mg of vortioxetine/capsule)

| Component | Mass (mg/capsule) |
| --- | --- |
| the crystalline form of vortioxetine hemihydrobromide of the present invention | 11.3 |
| lactose | 68.7 |
| corn starch | 66 |
| polyvidone K30 | 4 |

The preparation procedures of the capsules (scale: 10000 capsules) are as follows:
1) Dissolve povidone K30 in 50% (v/v) ethanol aqueous solution;
2) Pass the above crystalline vortioxetine hemihydrobromide through a 100-mesh sieve, and then mix well with lactose and corn starch; add the povidone K30 solution to the mixed powder to prepare a soft material, pass the soft material through a sieve with 20-40 meshes for granulation, and dry;
3) Modify the dried granules and fill in capsule shells.

Example 91

Capsules were prepared with the crystalline form of vortioxetine hemihydrobromide of the present invention as the active pharmaceutical ingredient. The strength was 150 mg/capsule containing 22.7 mg of the crystalline form of vortioxetine hemihydrobromide (equivalent to 20 mg of vortioxetine). See Table 5 for the detailed formula.

TABLE 5

Formula of capsules (20 mg of vortioxetine/capsule)

| Component | Mass (mg/capsule) |
| --- | --- |
| the crystalline form of vortioxetine hemihydrobromide of the present invention | 22.7 |
| lactose | 61.8 |
| corn starch | 61.5 |
| polyvidone K30 | 4 |

The preparation procedures of the capsules (scale: 10000 capsules) are as follows:
1) Dissolve povidone K30 in 50% (v/v) ethanol aqueous solution;
2) Pass the above crystalline vortioxetine hemihydrobromide through a 100-mesh sieve, and then mixing well with lactose and corn starch; add the povidone K30 solution to the mixed powder to prepare a soft material, pass the soft material through a sieve with 20-40 meshes for granulation, and dry;
3) Modify the dried granules and fill in capsule shells.

Example 92-104

Capsules were prepared with crystalline forms of other salts or solvate of vortioxetine in the present invention as the active pharmaceutical ingredient. The strength was 150 mg/capsule containing 10 mg or 20 mg of vortioxetine.

The formula is as follows: The crystalline form of vortioxetine hemihydrobromide in examples 90 and 91 was replaced by the crystalline vortioxetine hydrobromide isopropanol solvate of the present invention, the crystalline form B of vortioxetine besylate, the crystalline form C of vortioxetine citrate, the crystalline form S of vortioxetine succinate, the crystalline form T of vortioxetine p-toluenesulfonate, the crystalline form Ch of vortioxetine p-chlorobenzenesulfonate, the crystalline form E of vortioxetine ethanedisulfonate, the crystalline form G of vortioxetine α-ketoglutarate, the crystalline form N of vortioxetine 1,5-naphthalenedisulfonate, the crystalline form Na of vortioxetine 2-naphthalenesulfonate, the crystalline form H of vortioxetine 3-hydroxy-2-naphthoate, the crystalline form Hy of vortioxetine 1-hydroxy-2-naphthoate, and the crystalline form O of vortioxetine oxalate respectively. The molar content of vortioxetine in the crystalline form of each formula was the same as that of examples 90 and 91; fillers in each formula were the same as those of examples 90 and 91.

The preparation procedures of the capsules are the same as those of examples 90 and 91.

Example 105

Tablets were prepared with the crystalline form of vortioxetine hemihydrobromide of the present invention as the active pharmaceutical ingredient. The strength was 100 mg/tablet containing 2.8 mg of the crystalline vortioxetine hemihydrobromide (equivalent to 2.5 mg of vortioxetine). See Table 6 for the detailed formula.

TABLE 6

Formula of tablets(2.5 mg Vortioxetine/tablet)

| Component | Mass (mg/tablet) |
|---|---|
| the crystalline form of vortioxetine hemihydrobromide of the present invention | 2.8 |
| lactose | 48.6 |
| corn starch | 23.8 |
| polyvinylpyrrolidone | 3.4 |
| water | 9.7 |
| microcrystalline cellulose | 18 |
| croscarmellose sodium | 2.7 |
| magnesium stearate | 0.7 |

Preparation procedures of the tablets (scale: 10000 tablets) are as follows:
1) Pass the above crystalline vortioxetine hemihydrobromide through a 100-mesh sieve, pass magnesium stearate through a 60-mesh sieve and pass other solid excipients through a 80-mesh sieve respectively;
2) Mix well the sieved crystalline vortioxetine hemihydrobromide, lactose, corn starch, microcrystalline cellulose, polyvinylpyrrolidone and a ½ quantity of croscarmellose sodium in a mixer and granulate using water as the wetting agent.
3) Dry the wet granules in an oven until the water content is below 3%; add another ½ quantity of croscarmellose sodium and magnesium stearate to the dry granules and mix well. Analyze the active ingredient in the granules, determine the tablet target weight and then perform tabletting.

Example 106

Tablets were prepared with the crystalline form of vortioxetine hemihydrobromide of the present invention as the active pharmaceutical ingredient. The strength was 100 mg/tablet containing 14.2 mg of the crystalline vortioxetine hemihydrobromide (equivalent to 12.5 mg of vortioxetine). See Table 7 for the detailed formula.

TABLE 7

Formula of tablets (12.5 mg Vortioxetine/tablet)

| Component | Mass (mg/tablet) |
|---|---|
| the crystalline form of vortioxetine hemihydrobromide of the present invention | 14.2 |
| lactose | 38.2 |
| corn starch | 23 |
| polyvinylpyrrolidone | 3.4 |
| ethanol | 9.3 |
| microcrystalline cellulose | 17.8 |
| croscarmellose sodium | 2.7 |
| magnesium stearate | 0.7 |

Preparation procedures of the tablets (scale: 10000 tablets) are as follows:
1) Pass the above crystalline form of vortioxetine hemihydrobromide through a 100-mesh sieve, pass magnesium stearate through a 60-mesh sieve and pass other solid excipients through a 80-mesh sieve, respectively;
2) Mix well the sieved crystalline vortioxetine hemihydrobromide, lactose, corn starch, microcrystalline cellulose, polyvinylpyrrolidone and a ½ quantity of croscarmellose sodium in a mixer and granulate using ethanol as the wetting agent.
3) Dry the wet granules in an oven until the water content is below 3%; add another ½ quantity of croscarmellose sodium and magnesium stearate to the dry granules and mix well. Analyze the active ingredient in the granules, determine the tablet weight and then perform tabletting.

Example 107

Tablets were prepared with the crystalline form of vortioxetine hemihydrobromide of the present invention as the active pharmaceutical ingredient. The strength was 100 mg/tablet containing 22.7 mg of the crystalline form of vortioxetine hemihydrobromide (equivalent to 20 mg of vortioxetine). See Table 8 for the detailed formula.

TABLE 8

Formula of tablets (20 mg Vortioxetine/tablet)

| Component | Mass (mg/tablet) |
|---|---|
| the crystalline form of vortioxetine hemihydrobromide of the present invention | 22.7 |
| lactose | 39.2 |
| corn starch | 18.8 |
| polyvinylpyrrolidone | 2.6 |
| water | 7.4 |
| microcrystalline cellulose | 13.7 |
| croscarmellose sodium | 2.4 |
| magnesium stearate | 0.6 |

Preparation procedures of the tablets are the same as those of example 105.

Example 108

Tablets were prepared with the crystalline form of vortioxetine hemihydrobromide of the present invention as the active pharmaceutical ingredient. The strength was 100 mg/tablet containing 22.7 mg of the crystalline form of vortioxetine hemihydrobromide (equivalent to 20 mg of vortioxetine). See Table 9 for the detailed formula.

TABLE 9

Formula of tablets (20 mg Vortioxetine/tablet)

| Component | Mass (mg/tablet) |
|---|---|
| the crystalline form of vortioxetine hemihydrobromide of the present invention | 22.7 |
| mannitol | 38.5 |
| cornstarch | 15 |
| polyvinylpyrrolidone | 2.4 |
| ethanol | 8.2 |
| microcrystalline cellulose | 18.1 |
| sodium carboxymethylstarch | 2.9 |
| magnesium stearate | 0.4 |

Preparation procedures of the tablets are the same as those of example 106.

Example 109

Tablets were prepared with the crystalline form of vortioxetine hemihydrobromide of the present invention as the active pharmaceutical ingredient. The strength was 100 mg/tablet containing 11.3 mg of the crystalline form of vortioxetine hemihydrobromide (equivalent to 10 mg of vortioxetine). See Table 10 for the detailed formula.

TABLE 10

Formula of tablets (10 mg Vortioxetine/tablet)

| Component | Mass (mg/tablet) |
| --- | --- |
| the crystalline form of vortioxetine hemihydrobromide of the present invention | 11.3 |
| mannitol | 43 |
| corn starch | 19.6 |
| polyvinylpyrrolidone | 3.2 |
| ethanol | 8.4 |
| microcrystalline cellulose | 19.4 |
| sodium carboxymethylstarch | 3.1 |
| magnesium stearate | 0.4 |

Preparation procedures of the tablets are the same as those of example 106.

Example 110

Tablets were prepared with the crystalline form of vortioxetine hemihydrobromide of the present invention as the active pharmaceutical ingredient. The strength was 100 mg/tablet containing 5.7 mg of the crystalline form of vortioxetine hemihydrobromide (equivalent to 5 mg of vortioxetine). See Table 11 for the detailed formula.

TABLE 11

Formula of tablets (5 mg Vortioxetine/tablet)

| Component | Mass (mg/tablet) |
| --- | --- |
| the crystalline form of vortioxetine hemihydrobromide of the present invention | 5.7 |
| mannitol | 42.5 |
| corn starch | 25.8 |
| polyvinylpyrrolidone | 3.2 |
| water | 8.8 |
| microcrystalline cellulose | 19.3 |
| sodium carboxymethylstarch | 3.1 |
| magnesium stearate | 0.4 |

Preparation procedures of the tablets are the same as those of example 105.

Example 111

Tablets were prepared with the crystalline form of vortioxetine hemihydrobromide of the present invention as the active pharmaceutical ingredient. The strength was 100 mg/tablet containing 2.8 mg of the crystalline form of vortioxetine hemihydrobromide (equivalent to 2.5 mg of vortioxetine). See Table 12 for the detailed formula.

TABLE 12

Formula of tablets (2.5 mg Vortioxetine/tablet)

| Component | Mass (mg/tablet) |
| --- | --- |
| the crystalline form of vortioxetine hemihydrobromide of the present invention | 2.8 |
| mannitol | 46.5 |
| corn starch | 24 |

TABLE 12-continued

Formula of tablets (2.5 mg Vortioxetine/tablet)

| Component | Mass (mg/tablet) |
| --- | --- |
| polyvinylpyrrolidone | 3.3 |
| water | 9.2 |
| microcrystalline cellulose | 20.0 |
| sodium carboxymethylstarch | 3.0 |
| magnesium stearate | 0.4 |

Preparation procedures of the tablets are the same as those of example 105.

Example 112

Tablets were prepared with the crystalline form of vortioxetine hemihydrobromide of the present invention as the active pharmaceutical ingredient. The strength was 100 mg/tablet containing 4.5 mg of the crystalline form of vortioxetine hemihydrobromide (equivalent to 4 mg of vortioxetine). See Table 13 for the detailed formula.

TABLE 13

Formula of tablets (4 mg Vortioxetine/tablet)

| Component | Mass (mg/tablet) |
| --- | --- |
| the crystalline form of vortioxetine hemihydrobromide of the present invention | 4.5 |
| anhydrous calcium hydrophosphate | 45.6 |
| corn starch | 23.4 |
| copolyvidone | 3.1 |
| ethanol | 9.3 |
| microcrystalline cellulose | 20.0 |
| sodium carboxymethylstarch | 3.0 |
| magnesium stearate | 0.4 |

Preparation procedures of the tablets are the same as those of example 106.

Example 113~125

By reference to the formulas of examples 105 to 112, tablets were prepared with crystalline forms of other salts or solvate of vortioxetine in the present invention as the active pharmaceutical ingredient. The strength was 100 mg/tablet containing 2.5 mg, 12.5 mg, 20 mg, 10 mg, 5 mg, 2.5 mg or 4 mg of vortioxetine.

The formula is as follows: The crystalline form of vortioxetine hemihydrobromide in examples 105 to 112 was replaced by the crystalline vortioxetine hydrobromide isopropanol solvate of the present invention, the crystalline form B of vortioxetine besylate, the crystalline form C of vortioxetine citrate, the crystalline form S of vortioxetine succinate, the crystalline form T of vortioxetine p-toluenesulfonate, the crystalline form Ch of vortioxetine p-chlorobenzenesulfonate, the crystalline form E of vortioxetine ethanedisulfonate, the crystalline form G of vortioxetine α-ketoglutarate, the crystalline form N of vortioxetine 1,5-naphthalenedisulfonate, the crystalline form Na of vortioxetine 2-naphthalenesulfonate, the crystalline form H of vortioxetine 3-hydroxy-2-naphthoate, the crystalline form Hy of vortioxetine 1-hydroxy-2-naphthoate, and the crystalline form O of vortioxetine oxalate respectively. The molar content of vortioxetine in each formula was the same as that in examples 105 to 112; fillers in each formula were the same as those of examples 105 to 112.

Preparation procedures of the tablets are the same as those in examples 105 to 112.

Example 126

An oral suspension was prepared with the crystalline form of vortioxetine hemihydrobromide of the present invention as the active pharmaceutical ingredient. The strength was 50 mL/vial containing 113 mg of the crystalline form of vortioxetine hemihydrobromide (equivalent to 100 mg of vortioxetine).

The formula of the oral suspension is as follows:
the crystalline form of vortioxetine hemihydrobromide of the present invention: 2.2 g (equivalent to 2 g of vortioxetine)
xanthan gum: 8 g
sodium dihydrogen citrate: 2 g
methyl p-hydroxybenzoate: 1.4 g
simple syrup: 150 mL
orange essence: 1 mL
water: q.s. to 1000 mL Preparation procedures of the oral suspension is as follows:
Mix the crystalline form of vortioxetine hemihydrobromide of the present invention, xanthan gum, sodium dihydrogencitrate, methyl p-hydroxybenzoate, simple syrup and orange essence, and add water to 1000 mL mark to prepare 50 vials.

Example 127~139

An oral suspension was prepared with crystalline forms of other salts of vortioxetine of the present invention as the active pharmaceutical ingredient. The strength was 50 mL/vial containing the API equivalent to 100 mg of vortioxetine.

The formula is as follows: By reference to the formula in example 126, the crystalline form of vortioxetine hemihydrobromide in example 126 was replaced by the vortioxetine hydrobromide isopropanol solvate of the present invention, the crystalline form B of vortioxetine besylate, the crystalline form C of vortioxetine citrate, the crystalline form S of vortioxetine succinate, the crystalline form T of vortioxetine p-toluenesulfonate, the crystalline form Ch of vortioxetine p-chlorobenzenesulfonate, the crystalline form E of vortioxetine ethanedisulfonate, the crystalline form G of vortioxetine α-ketoglutarate, the crystalline form N of vortioxetine 1,5-naphthalenedisulfonate, the crystalline form Na of vortioxetine 2-naphthalenesulfonate, the crystalline form H of vortioxetine 3-hydroxy-2-naphthoate, the crystalline form Hy of vortioxetine 1-hydroxy-2-naphthoate, and the crystalline form O of vortioxetine oxalate, respectively. The molar content of vortioxetine in each formula was the same as that in example 126; fillers in each formula were the same as those in example 126.

The preparation procedures of the oral suspensions are the same as those in example 126.

Example 140

The crystalline form of vortioxetine hemihydrobromide of the present invention, the β Form of vortioxetine hydrobromide prepared in preparation example 2 and the β Form of vortioxetine hydrobromide containing 20% of the crystalline form of vortioxetine hemihydrobromide of the present invention were tableted by the method in example 105 and then subjected to phase stability comparison.

Dissolution was determined by reference to the dissolution conditions of Benorilate Tablets described in 2010 Chinese Pharmacopoeia. The paddle method was used with the paddle rotation speed at 50 r/min. 900 mL of water was the dissolution medium. The temperature was 37° C. Take 3 mL of the dissolution medium for sampling at 2, 10, 20, 40 and 60 min respectively. Each time after sampling, 3 mL of water was added back to dissolution medium to supplement the volume. The concentration of the dissolution medium at each time point was measured by HPLC, and the dissolution profile was plotted.

Figure 11:
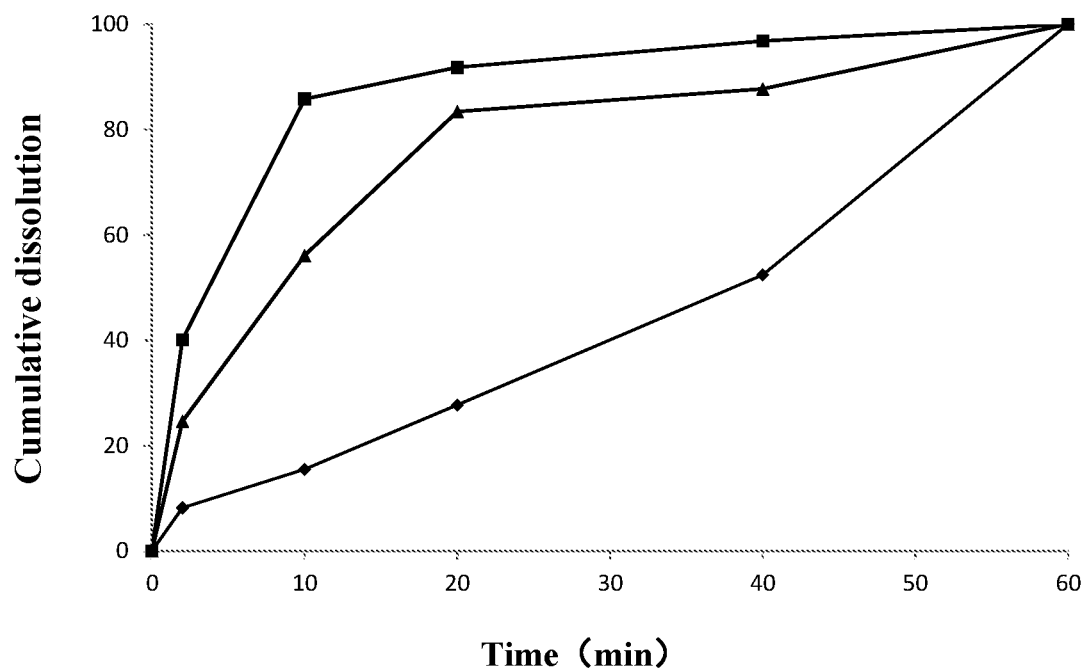
FIG. 11 is a comparison plot of dissolution profiles of the vortioxetine hemihydrobromide crystalline form of the present invention (♦), the β Form of vortioxetine hydrobromide (■) and the β Form of vortioxetine hydrobromide containing 20% of the vortioxetine hemihydrobromide crystalline form of the present invention (▲).

It is known to those skilled in the art that it is very important to maintain stability of single crystalline form during pharmaceutical development and storage. It can be known from the dissolution data and the dissolution profiles shown in Table 14 and FIG. 11 that, compared to pure crystalline forms (e.g. the crystalline form of vortioxetine hemihydrobromide of the present invention or the β Form of vortioxetine hydrobromide), the mixed crystalline forms (e.g. the β Form of vortioxetine hydrobromide mixed with 20% of the crystalline form of vortioxetine hemihydrobromide of the present invention) has different dissolution behaviors, resulted in varied product quality. Example 88 showed that the known β Form of vortioxetine hydrobromide completely transformed to the crystalline vortioxetine hemihydrobromide of the present invention in the presence of ethanol or water. Therefore, when the known β Form of vortioxetine hydrobromide is used as the active pharmaceutical ingredient for formulation, its crystalline form may change during production and storage due to the presence of ethanol or water, causing product quality variations; In the contrast, the crystalline form of vortioxetine hemihydrobromide of the present invention is stable, keeping its crystalline form unchanged under routine conditions or in presence of ethanol or water. Therefore, the crystalline form of vortioxetine hemihydrobromide of the present invention is more suitable for the wet granulation process of solid formulations or preparation of oral suspensions.

TABLE 14

| | Comparison of dissolution data | | | | | |
|---|---|---|---|---|---|---|
| | the crystalline form of vortioxetine hemihydrobromide of the present invention | | the β Form of vortioxetine hydrobromide | | the β Form of vortioxetine hydrobromide mixed with 20% of the crystalline form of vortioxetine hemihydrobromide of the present invention | |
| Sampling time (min) | Concentration (mg/ml) | Cumulative dissolution (%) | Concentration (mg/ml) | Cumulative dissolution (%) | Concentration (mg/ml) | Cumulative dissolution (%) |
| 2 | 0.00227 | 8.2 | 0.01312 | 40.1 | 0.00758 | 24.6 |
| 10 | 0.00432 | 15.5 | 0.02805 | 85.8 | 0.01726 | 56.1 |
| 20 | 0.00772 | 27.7 | 0.03002 | 91.8 | 0.02565 | 83.4 |

TABLE 14-continued

Comparison of dissolution data

| Sampling time (min) | the crystalline form of vortioxetine hemihydrobromide of the present invention | | the β Form of vortioxetine hydrobromide | | the β Form of vortioxetine hydrobromide mixed with 20% of the crystalline form of vortioxetine hemihydrobromide of the present invention | |
|---|---|---|---|---|---|---|
| | Concentration (mg/ml) | Cumulative dissolution (%) | Concentration (mg/ml) | Cumulative dissolution (%) | Concentration (mg/ml) | Cumulative dissolution (%) |
| 40 | 0.01133 | 52.4 | 0.03166 | 96.8 | 0.02697 | 87.7 |
| 60 | 0.02786 | 100.0 | 0.03342 | 100.0 | 0.02786 | 100.0 |

Example 141

Sustained-release tablets were prepared with the crystalline form of vortioxetine hemihydrobromide of the present invention as the active pharmaceutical ingredient. The strength was 100 mg/tablet containing 2.8 mg of the crystalline form of vortioxetine hemihydrobromide (equivalent to 2.5 mg of vortioxetine). See Table 15 for the detailed formula.

TABLE 15

Formula of sustained-release tablets (2.5 mg Vortioxetine/tablet)

| Component | Mass (mg/tablet) |
|---|---|
| the crystalline form of vortioxetine hemihydrobromide of the present invention | 2.8 |
| lactose | 48.6 |
| hypromellose | 33.5 |
| polyvinylpyrrolidone | 3.4 |
| microcrystalline cellulose | 18 |
| croscarmellose sodium | 2.7 |
| magnesium stearate | 0.7 |

Preparation procedures of the sustained-release tablets (scale: 10000 tablets) are as follows:
1) Pass the above crystalline form of vortioxetine hemihydrobromide through a 100-mesh sieve, pass magnesium stearate through a 60-mesh sieve and pass other solid excipients through a 80-mesh sieve, respectively;
2) Mix well the sieved crystalline vortioxetine hemihydrobromide, lactose, hypromellose, microcrystalline cellulose, polyvinylpyrrolidone, magnesium stearate, and croscarmellose sodium in a mixer. Analyze the active ingredient in the granules, determine the tablet weight and then perform tabletting.

Example 142

Sustained-release tablets were prepared with the crystalline form of vortioxetine hemihydrobromide of the present invention as the active pharmaceutical ingredient. The strength was 100 mg/tablet containing 11.3 mg of the crystalline form of vortioxetine hemihydrobromide (equivalent to 10 mg of vortioxetine). See Table 16 for the detailed formula.

TABLE 16

Formula of sustained-release tablets (10 mg Vortioxetine/tablet)

| Component | Mass (mg/tablet) |
|---|---|
| the crystalline form of vortioxetine hemihydrobromide of the present invention | 11.3 |
| mannitol | 43 |
| hypromellose | 28 |
| polyvinylpyrrolidone | 3.2 |
| microcrystalline cellulose | 19.4 |
| sodium carboxymethylstarch | 3.1 |
| magnesium stearate | 0.4 |

Preparation procedures of the sustained-release tablets are the same as those of example 141.

Example 143

Sustained-release tablets were prepared with the crystalline form of vortioxetine hemihydrobromide of the present invention as the active pharmaceutical ingredient. The strength was 100 mg/tablet containing 22.7 mg of the crystalline form of vortioxetine hemihydrobromide (equivalent to 20 mg of vortioxetine). See Table 17 for the detailed formula.

TABLE 17

Formula of sustained-release tablets (10 mg Vortioxetine/tablet)

| Component | Mass (mg/tablet) |
|---|---|
| the crystalline form of vortioxetine hemihydrobromide of the present invention | 22.7 |
| lactose | 39.2 |
| hypromellose | 26.2 |
| polyvinylpyrrolidone | 2.6 |
| microcrystalline cellulose | 13.7 |
| croscarmellose sodium | 2.4 |
| magnesium stearate | 0.6 |

Preparation procedures of the sustained-release tablets are the same as those of example 141.

Example 144

Dissolution comparison of the sustained-release tablets.
The crystalline form of vortioxetine hemihydrobromide of the present invention and the β Form of vortioxetine hydrobromide prepared in preparation example 2 were tableted by the method of example 141 and then subjected to dissolution comparison.
Water was used as the dissolution medium. Parameter setting of the dissolution tester: The temperature was 37° C.

The rotate speed of the stirring paddle was 50 r/min. Take 3 ml of the dissolution medium out at 0.5, 1, 2, 6 and 12 hours respectively. Each time after sampling, 3 mL of water was added back to the dissolution medium to supplement the volume. The concentration of the dissolution medium at each time point was determined by HPLC.

The results shown in Table 18 indicated that the sustained tablets prepared with the crystalline form of vortioxetine hemihydrobromide of the present invention had cumulative dissolution 14.3% at 1 hour and 58.5% at 6 hours; while the tablets prepared with the β Form of vortioxetine hydrobromide had cumulative dissolution 50.0% at 0.5 hours and showed a significant burst release. Therefore, compared to the β Form of vortioxetine hydrobromide, the crystalline form of vortioxetine hemihydrobromide of the present invention is more suitable for preparation of sustained-release formulations.

TABLE 18

Comparison of dissolution data

| Sampling time (hours) | the crystalline form of vortioxetine hemihydrobromide of the present invention | | the β Form of vortioxetine hydrobromide | |
|---|---|---|---|---|
| | Concentration (mg/ml) | Cumulative dissolution (%) | Concentration (mg/ml) | Cumulative dissolution (%) |
| 0.5 | 0.00225 | 8.1 | 0.01637 | 50.0 |
| 1 | 0.00398 | 14.3 | 0.02971 | 90.9 |
| 2 | 0.00765 | 27.4 | 0.03081 | 94.2 |
| 6 | 0.01264 | 58.5 | 0.03156 | 96.5 |
| 12 | 0.02633 | 94.5 | 0.03342 | 100.0 |

Abovementioned are only embodiments of the present invention, which do not cover the entire protection scope of the present invention. Based on the technical disclosure of the present invention, modifications or replacements envisaged by those skilled in the art without creative labor should all be within the protection scope of the present invention. Therefore, the protection scope of the present invention shall be subject to that defined by the claims.

The invention claimed is:

1. Vortioxetine hemihydrobromide represented by formula (I):

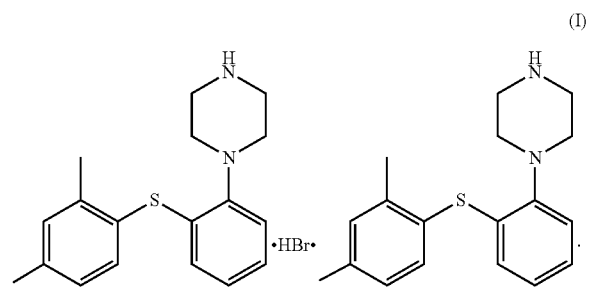

(I)

2. A preparation method of the vortioxetine hemihydrobromide according to claim 1, which comprises the following procedures: respectively preparing solutions of vortioxetine and hydrobromic acid in solvents, wherein the molar ratio of vortioxetine to hydrobromic acid is 10:1-2:1; mixing the two solutions to produce a suspension and stirring, then removing the solvents by rotary evaporation to obtain the vortioxetine hemihydrobromide; wherein the solvents are selected from the group consisting of alcohols, esters, ketones and mixtures thereof.

3. The vortioxetine hemihydrobromide according to claim 1 in a crystalline form, which is characterized in that, measured with Cu-Kα radiation, the X-ray powder diffraction pattern of the crystalline form of vortioxetine hemihydrobromide, expressed as 2θ angles, has the following characteristic peaks: 4.3±0.2°, 14.9±0.2°, 17.8±0.2°, 18.9±0.2°, 19.4±0.2° and 22.8±0.2°.

4. The vortioxetine hemihydrobromide according to claim 3, which is characterized in that, measured with Cu-Kα radiation, the X-ray powder diffraction pattern of the crystalline form of vortioxetine hemihydrobromide, expressed as 2θ angles, has the following characteristic peaks: 4.3±0.2°, 14.9±0.2°, 17.1±0.2°, 17.8±0.2°, 18.9±0.2°, 19.4±0.2°, 22.0±0.2°, 22.4±0.2°, 22.8±0.2°, 24.4±0.2°, 25.4±0.2° and 29.7±0.2°.

5. The vortioxetine hemihydrobromide according to claim 4, which is characterized in that, the X-ray powder diffraction pattern of the crystalline form of vortioxetine hemihydrobromide, expressed as 2θ angles, has the following characteristic peaks with the following relative intensities:

| Diffraction angle 2θ | Relative intensity % |
|---|---|
| 4.3 ± 0.2° | 25.6 |
| 14.9 ± 0.2° | 23.3 |
| 16.8 ± 0.2° | 11.2 |
| 17.1 ± 0.2° | 17.6 |
| 17.8 ± 0.2° | 100.0 |
| 18.9 ± 0.2° | 22.5 |
| 19.4 ± 0.2° | 49.5 |
| 22.0 ± 0.2° | 24.5 |
| 22.4 ± 0.2° | 16.7 |
| 22.8 ± 0.2° | 31.8 |
| 24.4 ± 0.2° | 17.7 |
| 25.4 ± 0.2° | 15.6 |
| 25.9 ± 0.2° | 10.1 |
| 27.8 ± 0.2° | 11.8 |
| 28.6 ± 0.2° | 11.1 |
| 29.0 ± 0.2° | 10.3 |
| 29.7 ± 0.2° | 24.0 |
| 31.3 ± 0.2° | 12.9. |

6. The vortioxetine hemihydrobromide according to claim 3, which is characterized in that, the Fourier infrared spectrum of the crystalline form of vortioxetine hemihydrobromide has characteristic peaks at the wave numbers of 3171, 2952, 2916, 2828, 2808, 2733, 1580, 1474, 1439, 1146, 1053, 924, 861 and 735 $cm^{-1}$.

7. A preparation method of the vortioxetine hemihydrobromide according to claim 3, which comprises the following procedures: respectively preparing solution systems of vortioxetine and hydrobromic acid in solvents, wherein the solvents are selected from the group consisting of $C_1$-$C_4$ alcohols, $C_4$-$C_5$ esters, $C_3$-$C_4$ ketones and mixtures thereof, the molar ratio of vortioxetine to hydrobromic acid in the two solution systems is 10:1-2:1; mixing the two solution systems to produce a suspension and stirring to crystallize for 1-48 hours at a crystallization temperature of -10-50° C., then removing the solvents to obtain the crystalline form of vortioxetine hemihydrobromide.

8. The preparation method of the vortioxetine hemihydrobromide according to claim 7, which is characterized in that, the solvents are selected from the group consisting of ethanol, isopropanol, ethyl acetate and acetone, the molar ratio of vortioxetine to hydrobromic acid is 4:1-2:1, the crystallization temperature is room temperature, and the duration of crystallization is 2-4 hours.

9. The preparation method of the crystalline form of vortioxetine hemihydrobromide according to claim 7, which is characterized in that, the concentration of vortioxetine in the solvent is 0.1-1 times of its solubility in the solvent at the crystallization temperature.

10. The preparation method of the crystalline form of vortioxetine hemihydrobromide according to claim 9, which is characterized in that, the concentration of vortioxetine in the solvent is 0.5-1 times of its solubility in the solvent at the crystallization temperature.

11. The preparation method of the crystalline form of vortioxetine hemihydrobromide according to claim 7, which is characterized in that, the concentration of hydrobromic acid in the solvent is 0.5-1 times of its solubility in the solvent at the crystallization temperature.

12. A pharmaceutical composition, which comprises a therapeutically and/or preventively effective amount of the vortioxetine hemihydrobromide according to claim 1 and at least one pharmaceutically acceptable excipient.

13. The pharmaceutical composition according to claim 12, which is characterized in that, the pharmaceutical composition is in a dosage form selected from the group consisting of tablets, capsules, granules, pulvis, pills, powder, lozenges, syrups and suspensions by oral administration, and aqueous solutions, non-aqueous solutions and emulsions for injection by parenteral administration.

14. The pharmaceutical composition according to claim 13, which is characterized in that, the pharmaceutical composition is selected from the group consisting of tablets, capsules and suspensions by oral administration.

15. The pharmaceutical composition according to claim 14, which is characterized in that, the tablets or the capsules by oral administration are prepared by wet granulation processes.

16. A method of treating a disease selected from the group consisting of affective disorders, major depression, routine anxiety disorder, obsessive compulsive disorder, panic disorder, post-traumatic stress disorder, depressions associated with cognitive deficits, Alzheimer's disease and anxiety disorder, depression with residual symptoms, chronic pain, eating disorders, alcoholism, nicotine or carbohydrate addiction, drug abuse, alcohol and drug abuse, which comprises administering to a patient in need a therapeutically and/or preventively effective amount of the vortioxetine hemihydrobromide according to claim 1.

17. A pharmaceutical composition, which comprises a therapeutically and/or preventively effective amount of the vortioxetine hemihydrobromide according to claim 3 and at least one pharmaceutically acceptable excipient.

18. The pharmaceutical composition according to claim 17, which is characterized in that, the pharmaceutical composition is in a dosage form selected from the group consisting of tablets, capsules, granules, pulvis, pills, powder, lozenges, syrups and suspensions by oral administration, and aqueous solutions, non-aqueous solutions and emulsions for injection by parenteral administration.

19. The pharmaceutical composition according to claim 18, which is characterized in that, the pharmaceutical composition is selected from the group consisting of tablets, capsules and suspensions by oral administration.

20. The pharmaceutical composition according to claim 19, which is characterized in that the tablets or the capsules by oral administration are prepared by wet granulation processes.

* * * * *